United States Patent [19]

Nagano et al.

[11] Patent Number: 5,643,923

[45] Date of Patent: Jul. 1, 1997

[54] QUINUCLIDINYLOXY-ISOXAZOLE COMPOUNDS AND THEIR THERAPEUTIC USES

[75] Inventors: Mitsuo Nagano; Takeo Kobayashi; Junichi Sakai; Masao Kozuka; Nobuyoshi Iwata; Yoshiko Kubo, all of Tokyo, Japan

[73] Assignee: Sankyo Company, Limited, Tokyo, Japan

[21] Appl. No.: 937,445

[22] Filed: Aug. 27, 1992

Related U.S. Application Data

[63] Continuation of Ser. No. 694,447, May 1, 1991, abandoned.

[30] Foreign Application Priority Data

| May 11, 1990 | [JP] | Japan | 2-119754 |
| Aug. 17, 1990 | [JP] | Japan | 2-216519 |
| Oct. 17, 1990 | [JP] | Japan | 2-278489 |

[51] Int. Cl.$^6$ ............... A61K 31/42; A61K 31/44; C07D 453/02; C07D 261/04
[52] U.S. Cl. .......... 514/305; 546/133; 546/137; 514/380; 548/241; 548/243; 548/247
[58] Field of Search ............ 546/133, 137; 514/305, 380; 548/241, 243, 247

[56] References Cited

U.S. PATENT DOCUMENTS

| 3,290,301 | 12/1966 | Kano et al. | 514/133 |
| 5,116,839 | 5/1992 | Iwata et al. | 514/236.8 |
| 5,321,037 | 6/1994 | Nagano et al. | 514/379 |

FOREIGN PATENT DOCUMENTS

| 254868 | 6/1967 | Austria . |
| 0239309 | 9/1987 | European Pat. Off. . |
| 0273744 | 7/1988 | European Pat. Off. . |
| 306148 | 3/1989 | European Pat. Off. . |
| 0334674 | 9/1989 | European Pat. Off. . |
| 0335723 | 10/1989 | European Pat. Off. . |
| 0405905 | 1/1991 | European Pat. Off. . |
| 458214 | 11/1991 | European Pat. Off. . |

OTHER PUBLICATIONS

Chemical Abstracts vol. 68, No. 11, 11 Mar. 1968, p. 4788, abstract No. 49489j, Columbus, Ohio, US; K. Bowden et al.: "Synthesis of pantherine and related compounds" & J. Chem. Soc., C 1968, No. 2, pp. 172–185.

European Journal of Pharmacology vol. 130, Nos. 1/2, 1986, pp. 125–131; P. Sauerberg et al.: "Pharmacological profile of a novel class of muscarinic acetylcholine receptor agonists".

K. Bowden et al, "The Synthesis of Pantherine and Related Compounds", J. Chem. Soc. 1968, pp. 172–185.

Derwent Abstract of EP 458,214, 1991.

*Primary Examiner*—Shean C. Wu
*Attorney, Agent, or Firm*—Firshauf, Holtz, Goodman, Langer & Chick, P.C.

[57] ABSTRACT

Compounds of formula (I):

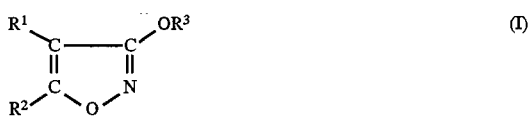

wherein $R^1$ is hydrogen, halogen or alkyl; $R^2$ is hydrogen, alkyl, optionally substituted phenyl or a heterocycle; or $R^1$ and $R^2$ together form a group of formula —$CR^4$=$CR^5$—$CR^6$=$CR^7$—, where $R^4$, $R^5$, $R^6$ and $R^7$ are hydrogen, halogen, alkyl group, alkoxy, halomethyl, alkylamino, dialkylamino, hydroxy, nitro, aliphatic carboxylic acylamino or amino; and $R^3$ is piperidyl, substituted piperidyl or quinuclidinyl. The compounds are useful in the treatment and prophylaxis of cognitive disorders, notably senile dementia, including Alzheimer's disease. Processes for preparing the compounds are also provided.

48 Claims, No Drawings

QUINUCLIDINYLOXY-ISOXAZOLE COMPOUNDS AND THEIR THERAPEUTIC USES

This application is a continuation of application Ser. No. 07/694,447, filed May 1, 1991, now abandoned.

BACKGROUND OF THE INVENTION

The present invention relates to a series of new piperidyloxyisoxazole and quinuclidinyloxyisoxazole derivatives which are useful for the treatment and prophylaxis of various disorders, notably senile dementia (including Alzheimer's disease). The invention also provides methods and compositions using these compounds as well as processes for preparing them.

In recent years, the number of elderly in the population has substantially increased, and there has been a corresponding increase in the number of age-related diseases and disorders, most notably senile dementia, including Alzheimer's disease. Senile dementia is a serious and growing problem in the world today, which can cause much discomfort and distress not only to the sufferer but also to relatives and to those responsible for them, and much research effort has been directed to attempts to cure or alleviate the condition. In particular Alzheimer's disease, in which senile dementia appears to afflict the patient prematurely, is a cause of much distress. Since the causes of senile dementia and Alzheimer's disease are presently unknown, treatment is difficult to develop and generally has to be confined merely to the relief of symptoms.

It is known that a characteristic exhibited by patients suffering from senile dementia is a decrease in the cerebral microcirculation and a reduction in cerebral metabolism, which together lead to dysfunction of cognition. Also, the early stages of senile dementia are generally accompanied by depression, and the relief of that depression would lead to an improvement in the quality of life of the sufferer.

Acetylcholine is a chemical transmitter having a wide range of activities in the body, and interference with its production and/or activity has been shown to result in a number of disorders. It has been found in patients suffering from senile dementia, including Alzheimer's disease, that the biosynthesis of acetylcholine in the brain is defective; however, even in such patients, receptors for acetylcholine in the brain may be much less affected, and they may still be functioning satisfactorily. The receptors for acetylcholine located on the pre-synaptic terminals in the brain are $M_2$ receptors, while those located on the post-synaptic membranes in the brain are $M_1$ and $M_3$ receptors. The $M_2$ receptors are abundant on the pre- and post-synapses of the heart, whilst many $M_1$ receptors are located in the cerebral cortex and hippocampus of the brain, which play an important role in memory and cognition. Accordingly, if the $M_1$ receptors could be stimulated during the early stages of the development of the dementia, it would be possible to alleviate the symptoms of the dementia and possibly prevent further decline. On the other hand, it is more desirable that any agent developed to stimulate the $M_1$ receptors should not correspondingly stimulate the $M_2$ receptors, since $M_2$ receptors inhibit the release of acetylcholine, and that they should minimise side-effects caused by stimulation of the heart.

We have now discovered a series of new piperidyloxyisoxazole and quinuclidinyloxyisoxazole derivatives which have been found to bind selectively to $M_1$ receptors, while binding to a much lesser extent to $M_2$ receptors and which, therefore, as explained above, are of value for the treatment and prophylaxis of senile dementia, including Alzheimer's disease.

Surprisingly, we have found that the compounds of the present invention also bind to $5\text{-}HT_3$ receptors and thus interfere with $5\text{-}HT_3$ activity. Since it is known that $5\text{-}HT_3$ antagonists have anti-anxiety, anti-depressant and anti-psychotic activities, the compounds of the present invention are also expected to be of value more widely in the treatment of patients having anxiety, depression and psychosis.

A number of isoxazole derivatives have previously been described by the present inventors and co-workers for use in the treatment and prophylaxis of a variety of diseases and disorders, including cerebrovascular disorders, as centrally acting muscle relaxants and as anti-depressants. These are disclosed, for example, in copending U.S. patent application Ser. No. 07/620 843, now abandoned filed 30th Nov. 1990, U.S. patent application Ser. No. 07/537 517, filed 13th Jun. 1990, now U.S. Pat. No. 5,116,839 and U.S. patent application Ser. No. 07/585 828, filed 20th Sep. 1990, now abandoned. Of these, the closest compounds structurally are disclosed in U.S. patent application Ser. No. 07/620 843, in which there are disclosed, inter alia, compounds of formula:

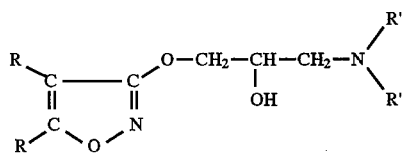

in which the symbols R each represent various groups and atoms and the symbols R' can represent various organic groups or, together with the nitrogen atom to which they are attached, can represent a heterocyclic group, including a piperidyl group. These prior art compounds differ from those of the present invention in that the piperidyl group represented by —NR'R' is necessarily attached to the remainder of the molecule via the nitrogen atom and, most importantly, by the presence in the prior art compounds of a group of formula:

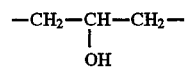

which has hitherto been considered essential to the desired activity, and which is totally absent in the compounds of the present invention.

BRIEF SUMMARY OF INVENTION

It is, therefore, an object of the present invention to provide a series of novel compounds which may be of value in the treatment and prophylaxis of senile dementia, including Alzheimer's disease.

It is a further object to provide compounds, certain of which are of more general use in the treatment and prophylaxis of cognitive disorders.

Other objects and advantages will become apparent as the description proceeds.

The compounds of the present invention are those compounds of formula (I):

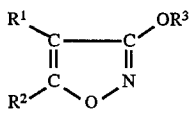

in which:

R¹ represents a hydrogen atom, a halogen atom or an alkyl group having from 1 to 6 carbon atoms;

R² represents: a hydrogen atom; an alkyl group having from 1 to 6 carbon atoms; a phenyl group which is unsubstituted or which is substituted by at least one of substituents (a), defined below; or a heterocyclic group which has 5 or 6 ring atoms, of which from 1 to 3 are hetero-atoms selected from the group consisting of nitrogen, oxygen and sulfur hetero-atoms, said heterocyclic group being unsubstituted or being substituted by at least one of substituents (a), defined below;

or

R¹ and R² together form a group of formula

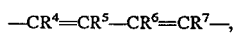

in which R⁴, R⁵, R⁶ and R⁷ are independently selected from the group consisting of: hydrogen atoms; halogen atoms; alkyl groups having from 1 to 6 carbon atoms; alkoxy groups having from 1 to 4 carbon atoms; halomethyl groups; alkylamino groups having from 1 to 4 carbon atoms; dialkylamino groups in which each alkyl group has from 1 to 4 carbon atoms; hydroxy groups; nitro groups; aliphatic carboxylic acylamino groups having from 2 to 4 carbon atoms; and amino groups; and R³ represents a piperidyl group, a substituted piperidyl group in which the nitrogen atom is substituted by an alkyl group having from 1 to 6 carbon atoms or a quinuclidinyl group;

substituents (a):

halogen atoms; alkyl groups having from 1 to 6 carbon atoms; alkoxy groups having from 1 to 6 carbon atoms; alkylamino groups having from 1 to 4 carbon atoms; dialkylamino groups in which each alkyl group has from 1 to 4 carbon atoms; hydroxy groups; nitro groups; and amino groups;

and pharmaceutically acceptable salts thereof.

The invention also provides a pharmaceutical composition for the treatment and prophylaxis of cognitive disorders comprising an effective amount of at least one active compound in admixture with a pharmaceutically acceptable carrier or diluent, wherein the active compound is selected from the group consisting of compounds of formula (I) and salts thereof, as defined above.

The invention further provides a method for the treatment or prophylaxis of cognitive disorders, anxiety, depression and psychosis, in a mammal, which may be human, comprising administering to said mammal an effective amount of at least one active compound, wherein the active compound is selected from the group consisting of compounds of formula (I) and salts thereof, as defined above.

The invention still further provides a method for the treatment or prophylaxis of senile dementia, including Alzheimer's disease, in a mammal, which may be human, comprising administering to said mammal an effective amount of at least one active compound, wherein the active compound is selected from the group consisting of compounds of formula (I) and salts thereof, as defined above.

The invention also provides processes for the preparation of the compounds of the invention, which are described in greater detail hereafter.

DETAILED DESCRIPTION OF INVENTION

In the compounds of the present invention, where R¹ represents a halogen atom, this may be a fluorine, chlorine, bromine or iodine atom, preferably a fluorine, chlorine or bromine atom.

Where R¹ and/or R² represents an alkyl group having from 1 to 6 carbon atoms, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, hexyl and isohexyl groups. Of these, we prefer those alkyl groups having from 1 to 4 carbon atoms, preferably the methyl, ethyl, propyl, isopropyl, butyl and isobutyl groups, and most preferably the methyl group.

Where R² represents a phenyl group, this may be substituted or unsubstituted. The substituted groups may be substituted by one or more of substituents (a), defined above and exemplified below. Where the group is substituted, there is no particular restriction on the number of substituents, except such as may be imposed by the number of substitutable positions and possibly by steric constraints, i.e. the maximum is 5 substituents for a phenyl group. However, in general, from 1 to 3 substituents are preferred. Examples of such substituents include:

halogen atoms, such as the fluorine, chlorine, bromine and iodine atoms;

alkyl groups having from 1 to 6, more preferably from 1 to 4, carbon atoms, such as the methyl, ethyl, propyl, isopropyl, butyl, isobutyl, sec-butyl and t-butyl groups, and most preferably the methyl group;

alkoxy groups having from 1 to 6, more preferably from 1 to 4 and most preferably 1 or 2, carbon atoms, such as the methoxy, ethoxy, propoxy, isopropoxy, butoxy, isobutoxy, sec-butoxy and t-butoxy groups, preferably the methoxy group;

alkylamino groups having from 1 to 4 carbon atoms, such as the methylamino, ethylamino, propylamino, isopropylamino, butylamino, isobutylamino, sec-butylamino and t-butylamino groups, preferably the methylamino group;

dialkylamino groups in which each alkyl group has from 1 to 4 carbon atoms, such as the dimethylamino, diethylamino, dipropylamino, diisopropylamino, dibutylamino, N-methyl-N-ethylamino, N-methyl-N-butyl, N-ethyl-N-propyl and N-ethyl-N-butyl groups;

hydroxy groups, nitro groups and amino groups.

Where R² represents a heterocyclic group, this has 5 or 6 ring atoms. Of these atoms, from 1 to 3 are hetero-atoms selected from the group consisting of nitrogen, oxygen and sulfur hetero-atoms. Where there are 3 hetero-atoms, we prefer that at least one (more preferably 2) should be a nitrogen atom and one or two should be nitrogen, oxygen or sulfur atoms (and, where there are two, they may be the same or different). Where there are two hetero-atoms, these may be the same or different and they are selected from nitrogen, oxygen and sulfur atoms; however, more preferably one is a nitrogen atom and the other is a nitrogen, oxygen or sulfur atom. Such groups may be unsubstituted or they may be substituted by at least one (preferably from 1 to 3) of substituents (a), defined and exemplified above. Examples of such unsubstituted groups include the furyl, thienyl, pyrrolyl, pyridyl, thiazolyl, isothiazolyl, oxazolyl, isoxazolyl, imidazolyl, pyrazolyl, pyranyl, pyrazinyl, pyridazinyl, pyrimidinyl, tetrahydrofuranyl, tetrahydrothienyl, pyrrolidinyl, thiazolidinyl, imidazolidinyl, imidazolinyl, oxazolinyl, oxazolidinyl, pyrazolidinyl, piperazyl, tetrahydropyrimidinyl, dihydropyridazinyl, morpholinyl, thiomorpholinyl, pyrrolidonyl, piperidonyl, pyridonyl, 2H-pyrrolyl, furazanyl and pyrazolinyl groups. Such groups may be unsubstituted or they may have at least one substituent selected from the group consisting of substituents (a), defined and exemplified above.

Alternatively, $R^1$ and $R^2$ may together form a group of formula —$CR^4$=$CR^5$—$CR^6$=$CR^7$—, in which $R^4$, $R^5$, $R^6$ and $R^7$ are as defined above, i.e. they form an optionally substituted benzene ring fused to the isoxazole system.

Where $R^4$, $R^5$, $R^6$ or $R^7$ represents a halogen atom, an alkyl group having from 1 to 6 carbon atoms, an alkoxy group having from 1 to 4 carbon atoms, an alkylamino group having from 1 to 4 carbon atoms or a dialkylamino group in which each alkyl group has from 1 to 4 carbon atoms, these may be as exemplified above in relation to the similar groups which are included in substituents (a). Where $R^4$, $R^5$, $R^6$ or $R^7$ represents a halomethyl group, this may be, for example, a chloromethyl, fluoromethyl, bromomethyl, iodomethyl, dichloromethyl, difluoromethyl, dibromomethyl, diiodomethyl, trichloromethyl, trifluoromethyl, tribromomethyl or triiodomethyl group, preferably a trifluoromethyl group. Where $R^4$, $R^5$, $R^6$ or $R^7$ represents an aliphatic carboxylic acylamino group having from 2 to 4 carbon atoms, this may be a straight or branched chain group and is preferably an alkanoylamino group; examples include the acetamido, propionamido, butyramido, isobutyramido, acrylamido, methacrylamido, propioloylamino and crotonoylamino groups.

$R^3$ may represent a substituted or unsubstituted piperidyl group or an unsubstituted quinclidinyl group which is preferably attached to the isoxazolyloxy group through a carbon atom. In the case of the substituted piperidyl group, the substituents are selected from the group consisting of alkyl groups having from 1 to 6, preferably from 1 to 4, carbon atoms, such as those exemplified above in relation to $R^1$ and $R^2$.

Preferred classes of compounds of the present invention include those compounds of formula (I) and salts thereof in which:

(A) $R^1$ represents a hydrogen atom, a halogen atom or an alkyl group having from 1 to 3 carbon atoms.

(B) $R^2$ represents: a hydrogen atom; an alkyl group having from 1 to 3 carbon atoms; a phenyl group which is unsubstituted or which is substituted by at least one of substituents (a'), defined below; or a heterocyclic group which has 5 or 6 ring atoms, of which from 1 to 3 are hetero-atoms selected from the group consisting of nitrogen, oxygen and sulfur hetero-atoms, said heterocyclic group being unsubstituted or being substituted by at least one of substituents (a'), defined below;

substituents (a'):
halogen atoms; alkyl groups having from 1 to 4 carbon atoms; alkoxy groups having from 1 to 4 carbon atoms; and hydroxy groups.

(C) $R^1$ and $R^2$ together form a group of formula

—$CR^4$=$CR^5$—$CR^6$=$CR^7$—, in which $R^4$, $R^5$, $R^6$ and $R^7$ are independently selected from the group consisting of hydrogen atoms; halogen atoms; alkyl groups having from 1 to 3 carbon atoms; alkoxy groups having from 1 to 3 carbon atoms; trifluoromethyl groups; and hydroxy groups.

(D) $R^3$ represents a piperidyl group, a substituted piperidyl group in which the nitrogen atom is substituted by an alkyl group having from 1 to 6 carbon atoms or a quinuclidinyl group.

Of these, we prefer those compounds of formula (I) and salts thereof in which $R^1$ and $R^2$ are as defined in (A) and (B) or in (C), and $R^3$ is as defined in (D), above.

More preferred classes of compounds of the present invention include those compounds of formula (I) and salts thereof in which:

(E) $R^1$ represents a hydrogen atom or a halogen atom.

(F) $R^2$ represents: a hydrogen atom; a phenyl group which is unsubstituted or which is substituted by at least one of substituents (a"), defined below; or a heterocyclic group which has 5 or 6 ring atoms, of which from 1 to 3, more preferably 1 or 2, are hetero-atoms selected from the group consisting of nitrogen, oxygen and sulfur hetero-atoms, said heterocyclic group being unsubstituted or being substituted by at least one of substituents (a"), defined below;

substituents (a"):
halogen atoms; alkoxy groups having from 1 to 4 carbon atoms; and hydroxy groups.

(G) $R^1$ and $R^2$ together form a group of formula

—$CR^4$=$CR^5$—$CR^6$=$CR^7$—, in which $R^4$, $R^5$, $R^6$ and $R^7$ are independently selected from the group consisting of hydrogen atoms, halogen atoms and hydroxy groups.

(H) $R^3$ represents a substituted piperidyl group in which the nitrogen atom is substituted by an alkyl group having from 1 to 6 carbon atoms or a quinuclidinyl group.

Of these, we prefer those compounds of formula (I) and salts thereof in which $R^1$ and $R^2$ are as defined in (E) and (F) or in (G), and $R^3$ is as defined in (H), above.

Examples of certain of the compounds of the present invention are shown by the following formulae (I-1) to (I-4), in which the symbols used in the formulae are as defined in the respective one of Tables 1 to 4, that is Table 1 relates to formula (I-1), Table 2 relates to formula (I-2), and so on. In Table 1, where the benzisoxazolyloxy group can be attached to the 2-, 3- or 4- positions of the piperidine ring, this is indicated by o-, m- or p-, respectively, so that, for example, the 2-isomer of Compound No. 18 is referred to as Compound No. 18o, the 3-isomer as 18m and so on. A similar convention is employed in Table 3. In the Tables, the following abbreviations are used:

| | |
|---|---|
| Bu | butyl |
| iBu | isobutyl |
| sBu | sec-butyl |
| tBu | t-butyl |
| Et | ethyl |
| Fur | furyl |
| Hx | hexyl |
| Me | methyl |
| Ph | phenyl |
| Pn | pentyl |
| Pr | propyl |
| iPr | isopropyl |
| Pyr | pyridyl |
| Thi | thienyl |

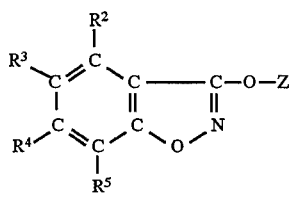
(I-1)

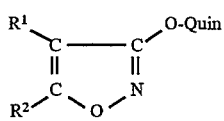
(I-2)

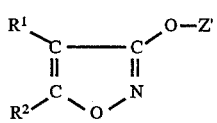
(I-3)

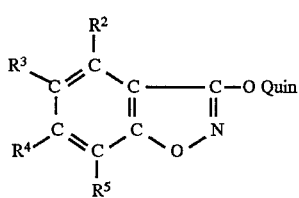
(I-4)

where Z represents:

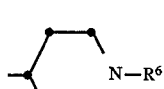 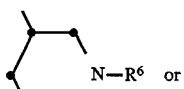 or

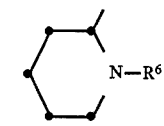

(referred to respectively as "p", "m" and "o"), Z' represents:

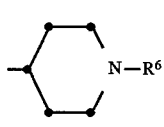 or 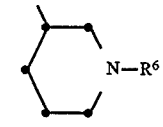

(referred to respectively as "p" and "m"), and "Quin" represents the quinuclidinyl group.

TABLE 1

| Cpd. No. | R⁶ | R² | R³ | R⁴ | R⁵ |
|---|---|---|---|---|---|
| 1-1o/m/p | H | H | Cl | H | H |
| 1-2o/m/p | Me | H | Cl | H | H |
| 1-3o/m/p | H | Cl | H | H | H |
| 1-4o/m/p | Me | Cl | H | H | H |
| 1-5o/m/p | H | H | H | Cl | H |
| 1-6o/m/p | Me | H | H | Cl | H |
| 1-7o/m/p | H | H | H | H | Cl |
| 1-8o/m/p | Me | H | H | H | Cl |
| 1-9o/m/p | H | Cl | Cl | H | H |
| 1-10o/m/p | Me | Cl | Cl | H | H |
| 1-11o/m/p | H | Cl | H | Cl | H |
| 1-12o/m/p | Me | Cl | H | Cl | H |
| 1-13o/m/p | H | Cl | H | H | Cl |
| 1-14o/m/p | Me | Cl | H | H | Cl |

TABLE 1-continued

| Cpd. No. | R⁶ | R² | R³ | R⁴ | R⁵ |
|---|---|---|---|---|---|
| 1-15o/m/p | H | H | Cl | Cl | H |
| 1-16o/m/p | Me | H | Cl | Cl | H |
| 1-17o/m/p | H | H | Cl | H | Cl |
| 1-18o/m/p | Me | H | Cl | H | Cl |
| 1-19o/m/p | H | H | H | Cl | Cl |
| 1-20o/m/p | Me | H | H | Cl | Cl |
| 1-21o/m/p | H | Cl | Cl | Cl | H |
| 1-22o/m/p | Me | Cl | Cl | Cl | H |
| 1-23o/m/p | H | Cl | Cl | H | Cl |
| 1-24o/m/p | Me | Cl | Cl | H | Cl |
| 1-25o/m/p | H | Cl | H | Cl | Cl |
| 1-26o/m/p | Me | Cl | H | Cl | Cl |
| 1-27o/m/p | H | H | Cl | Cl | Cl |
| 1-28o/m/p | Me | H | Cl | CE | Cl |
| 1-29o/m/p | H | C | Cl | C | Cl |
| 1-30o/m/p | Me | Cl | Cl | Cl | Cl |
| 1-31o/m/p | H | H | Br | H | H |
| 1-32o/m/p | Me | H | Br | H | H |
| 1-33o/m/p | H | H | F | H | H |
| 1-34o/m/p | Me | H | F | H | H |
| 1-35o/m/p | H | H | I | H | H |
| 1-36o/m/p | Me | H | I | H | H |
| 1-37o/m/p | H | H | OH | H | H |
| 1-38o/m/p | Me | H | OH | H | H |
| 1-39o/m/p | H | H | OMe | H | H |
| 1-40o/m/p | Me | H | OMe | H | H |
| 1-41o/m/p | H | H | OEt | H | H |
| 1-42o/m/p | Me | H | OEt | H | H |
| 1-43o/m/p | H | H | OPr | H | H |
| 1-44o/m/p | Me | H | OPr | H | H |
| 1-45o/m/p | H | H | OiPr | H | H |
| 1-46o/m/p | Me | H | OiPr | H | H |
| 1-47o/m/p | H | H | OBu | H | H |
| 1-48o/m/p | Me | H | OBu | H | H |
| 1-49o/m/p | H | H | OiBu | H | H |
| 1-50o/m/p | Me | H | OiBu | H | H |
| 1-51o/m/p | H | H | OsBu | H | H |
| 1-52o/m/p | Me | H | OsBu | H | H |
| 1-53o/m/p | H | H | OtBu | H | H |
| 1-54o/m/p | Me | H | OtBu | H | H |
| 1-55o/m/p | H | H | Me | H | H |
| 1-56o/m/p | Me | H | Me | H | H |
| 1-57o/m/p | H | H | Et | H | H |
| 1-58o/m/p | Me | H | Et | H | H |
| 1-59o/m/p | H | H | Pr | H | H |
| 1-60o/m/p | Me | H | Pr | H | H |
| 1-61o/m/p | H | H | iPr | H | H |
| 1-62o/m/p | Me | H | iPr | H | H |
| 1-63o/m/p | H | H | Bu | H | H |
| 1-64o/m/p | Me | H | Bu | H | H |
| 1-65o/m/p | H | H | iBu | H | H |
| 1-66o/m/p | Me | H | iBu | H | H |
| 1-67o/m/p | H | H | sBu | H | H |
| 1-68o/m/p | Me | H | sBu | H | H |
| 1-69o/m/p | H | H | tBu | H | H |
| 1-70o/m/p | Me | H | tBu | H | H |
| 1-71o/m/p | H | H | NH₂ | H | H |
| 1-72o/m/p | Me | H | NH₂ | H | H |
| 1-73o/m/p | H | H | NHMe | H | H |
| 1-74o/m/p | Me | H | NHMe | H | H |
| 1-75o/m/p | H | H | NHEt | H | H |
| 1-76o/m/p | Me | H | NHEt | H | H |
| 1-77o/m/p | H | H | NHPR | H | H |
| 1-78o/m/p | Me | H | NHPR | H | H |
| 1-79o/m/p | H | H | NHiPr | H | H |
| 1-80o/m/p | Me | H | NHiPr | H | H |
| 1-81o/m/p | H | H | NHBu | H | H |
| 1-82o/m/p | Me | H | NHBu | H | H |
| 1-83o/m/p | H | H | NHiBu | H | H |
| 1-84o/m/p | Me | H | NHiBu | H | H |
| 1-87o/m/p | H | H | NHtBu | H | H |
| 1-88o/m/p | Me | H | NHtBu | H | H |
| 1-89o/m/p | H | H | CF₃ | H | H |
| 1-90o/m/p | Me | H | CF₃ | H | H |
| 1-91o/m/p | Et | H | Cl | H | H |
| 1-92o/m/p | Et | H | Br | H | H |

TABLE 1-continued

| Cpd. No. | R⁶ | R² | R³ | R⁴ | R⁵ |
|---|---|---|---|---|---|
| 1-93o/m/p | Et | H | OH | H | H |
| 1-94o/m/p | Et | H | OMe | H | H |
| 1-95o/m/p | Et | H | OEt | H | H |
| 1-96o/m/p | Et | H | Me | H | H |
| 1-97o/m/p | Et | H | Pr | H | H |
| 1-98o/m/p | Et | H | Bu | H | H |
| 1-99o/m/p | Et | H | NH₂ | H | H |
| 1-100o/m/p | Et | H | NHMe | H | H |
| 1-101o/m/p | Et | H | NHEt | H | H |
| 1-102o/m/p | Et | H | CF₃ | H | H |
| 1-103o/m/p | Pr | H | Cl | H | H |
| 1-104o/m/p | Pr | H | Br | H | H |
| 1-105o/m/p | Pr | H | OH | H | H |
| 1-106o/m/p | Pr | H | OMe | H | H |
| 1-107o/m/p | Pr | H | OEt | H | H |
| 1-108o/m/p | Pr | H | Me | H | H |
| 1-109o/m/p | Pr | H | Pr | H | H |
| 1-110o/m/p | Pr | H | Bu | H | H |
| 1-111o/m/p | Pr | H | NH₂ | H | H |
| 1-112o/m/p | Pr | H | NHMe | H | H |
| 1-113o/m/p | Pr | H | NHEt | H | H |
| 1-114o/m/p | Pr | H | CF₃ | H | H |
| 1-115o/m/p | iPr | H | H | H |  |
| 1-116o/m/p | iPr | H | Br | H | H |
| 1-117o/m/p | iPr | H | OH | H | H |
| 1-118o/m/p | iPr | H | OMe | H | H |
| 1-119o/m/p | iPr | H | Me | H | H |
| 1-120o/m/p | iPr | H | Pr | H | H |
| 1-121o/m/p | iPr | H | NHMe | H | H |
| 1-122o/m/p | iPr | H | NHEt | H | H |
| 1-123o/m/p | iPr | H | CF₃ | H | H |
| 1-124o/m/p | Bu | H | Cl | H | H |
| 1-125o/m/p | Bu | H | Br | H | H |
| 1-126o/m/p | Bu | H | OH | H | H |
| 1-127o/m/p | Bu | H | OMe | H | H |
| 1-128o/m/p | Bu | H | Me | H | H |
| 1-129o/m/p | Bu | H | Pr | H | H |
| 1-130o/m/p | Bu | H | NHMe | H | H |
| 1-131o/m/p | Bu | H | NHEt | H | H |
| 1-132o/m/p | Bu | H | CF₃ | H | H |
| 1-133o/m/p | iBu | H | Cl | H | H |
| 1-134o/m/p | iBu | H | Br | H | H |
| 1-135o/m/p | iBu | H | OMe | H | H |
| 1-136o/m/p | iBu | H | Me | H | H |
| 1-137o/m/p | iBu | H | NHEt | H | H |
| 1-138o/m/p | iBu | H | CF₃ | H | H |
| 1-139o/m/p | sBu | H | Cl | H | H |
| 1-140o/m/p | sBu | H | OMe | H | H |
| 1-141o/m/p | tBu | H | Cl | H | H |
| 1-143o/m/p | Me | H | Cl | Br | H |
| 1-144o/m/p | Me | H | Cl | OMe | H |
| 1-145o/m/p | Me | H | Cl | Me | H |
| 1-146o/m/p | Me | H | Cl | NHMe | H |
| 1-147o/m/p | Me | H | Cl | CF₃ | H |
| 1-148o/m/p | Me | H | OMe | H | Me |
| 1-149o/m/p | Me | H | OMe | H | NHMe |
| 1-150o/m/p | Me | H | OMe | H | CF₃ |
| 1-151o/m/p | Me | NHMe | Me | H | H |
| 1-152o/m/p | Me | CF₃ | Me | H | H |
| 1-153o/m/p | Me | H | NHMe | H | CF₃ |
| 1-154o/m/p | Me | H | NHMe | H | OMe |
| 1-155o/m/p | Me | OMe | Cl | Br | H |
| 1-156o/m/p | Me | NHMe | Cl | Br | H |
| 1-157o/m/p | Me | Me | Cl | Br | H |
| 1-158o/m/p | Me | OMe | Cl | OMe | OMe |
| 1-159o/m/p | Me | Me | Cl | NHMe | NHMe |
| 1-160o/m/p | Me | Cl | Cl | Me | Me |
| 1-161o/m/p | H | H | NMe₂ | H | H |
| 1-162o/m/p | H | H | NEt₂ | H | H |
| 1-163o/m/p | H | H | NO₂ | H | H |
| 1-164o/m/p | H | H | NHCOMe | H | H |
| 1-165o/m/p | H | H | NHCOEt | H | H |
| 1-166o/m/p | H | H | NHCOPr | H | H |
| 1-167o/m/p | H | H | NHCOBu | H | H |
| 1-168o/m/p | H | H | NMePr | H | H |

TABLE 2

| Cpd. No. | R¹ | R² |
|---|---|---|
| 2-1 | H | H |
| 2-2 | H | Me |
| 2-3 | H | Et |
| 2-4 | H | Pr |
| 2-5 | H | iPr |
| 2-6 | H | Bu |
| 2-7 | H | iBu |
| 2-8 | H | sBu |
| 2-9 | H | tBu |
| 2-10 | H | p-ClPh |
| 2-11 | H | p-FPh |
| 2-12 | H | o-ClPh |
| 2-13 | H | p-MeOPh |
| 2-14 | H | m-MeOPh |
| 2-15 | H | o-MeOPh |
| 2-16 | H | 3,4-diMeOPh |
| 2-17 | H | p-HOPh |
| 2-18 | H | p-NO₂Ph |
| 2-19 | H | p-MeNHPh |
| 2-20 | Cl | H |
| 2-21 | Cl | Me |
| 2-22 | Cl | Et |
| 2-23 | Cl | Pr |
| 2-24 | Cl | iPr |
| 2-25 | Cl | Bu |
| 2-26 | Cl | iBu |
| 2-27 | Cl | sBu |
| 2-28 | Cl | tBu |
| 2-29 | Cl | p-ClPh |
| 2-30 | Cl | p-FPh |
| 2-31 | Cl | o-ClPh |
| 2-32 | Cl | p-MeOPh |
| 2-33 | Cl | m-MeOPh |
| 2-34 | Cl | o-MeOPh |
| 2-35 | Cl | 3,4-diMeOPh |
| 2-36 | Cl | p-HOPh |
| 2-37 | Cl | p-NO₂Ph |
| 2-38 | Cl | p-MeNHPh |
| 2-39 | Br | H |
| 2-40 | Br | Me |
| 2-41 | Br | p-CePh |
| 2-42 | F | H |
| 2-43 | F | Me |
| 2-44 | F | p-ClPh |
| 2-45 | Me | H |
| 2-46 | Me | Me |
| 2-47 | Me | Et |
| 2-48 | Me | Pr |
| 2-49 | Me | iPr |
| 2-50 | Me | Bu |
| 2-51 | Me | iBu |
| 2-52 | Me | sBu |
| 2-53 | Me | tBu |
| 2-54 | Me | p-ClPh |
| 2-55 | Me | m-ClPh |
| 2-56 | Me | p-FPh |
| 2-57 | Me | p-MeOPh |
| 2-58 | Me | m-MeoPh |
| 2-59 | Me | o-MeOPh |
| 2-60 | Me | 3,4-diMeOPh |
| 2-61 | Me | p-HOPh |
| 2-62 | Me | p-NO₂Ph |
| 2-63 | Me | p-MeNHPh |
| 2-64 | Et | H |
| 2-65 | Et | Me |
| 2-66 | Et | p-ClPh |
| 2-67 | Pr | H |
| 2-68 | Pr | Me |
| 2-69 | Pr | p-ClPh |
| 2-70 | iPr | H |
| 2-71 | iPr | Me |
| 2-72 | iPr | p-ClPh |
| 2-73 | Bu | H |
| 2-74 | Bu | Me |
| 2-75 | Bu | p-ClPh |
| 2-76 | iBu | H |

TABLE 2-continued

| Cpd. No. | R¹ | R² |
|---|---|---|
| 2-77 | iBu | Me |
| 2-78 | iBu | p-ClPh |
| 2-79 | sBu | H |
| 2-80 | sBu | Me |
| 2-81 | sBu | p-ClPh |
| 2-82 | tBu | H |
| 2-83 | tBu | Me |
| 2-84 | tBu | p-ClPh |
| 2-85 | Pn | H |
| 2-86 | Pn | Me |
| 2-87 | Pn | Pr |
| 2-88 | Pn | p-ClPh |
| 2-89 | Pn | p-FPh |
| 2-90 | Pn | p-MeOPh |
| 2-91 | Pn | p-HOPh |
| 2-92 | Pn | p-NO₂Ph |
| 2-93 | Pn | p-Me₂N—Ph |
| 2-94 | Hx | H |
| 2-95 | Hx | Me |
| 2-96 | Hx | p-ClPh |
| 2-97 | H | 2-Thi |
| 2-98 | Cl | 2-Thi |
| 2-99 | H | 3-Pyr |
| 2-100 | Cl | 3-Pyr |
| 2-101 | H | 2-Fur |
| 2-102 | Cl | 2-Fur |
| 2-103 | Cl | o-HOPh |
| 2-104 | Cl | m-HOPh |
| 2-105 | H | o-HOPh |
| 2-106 | H | m-HOPh |
| 2-107 | H | Ph |

TABLE 3

| Cpd. No. | R⁶ | R² | R⁴ |
|---|---|---|---|
| 3-1m/p | H | H | H |
| 3-2m/p | H | H | Me |
| 3-3m/p | H | H | Et |
| 3-4m/p | H | H | Pr |
| 3-5m/p | H | H | iPr |
| 3-6m/p | H | H | Bu |
| 3-7m/p | H | H | iBu |
| 3-8m/p | H | H | sBu |
| 3-9m/p | H | H | Pn |
| 3-10m/p | H | H | Hx |
| 3-11m/p | H | Me | H |
| 3-12m/p | H | Me | Me |
| 3-13m/p | H | Me | Et |
| 3-14m/p | H | Me | Pr |
| 3-15m/p | H | Me | iPr |
| 3-16m/p | H | Me | Bu |
| 3-17m/p | H | Me | iBu |
| 3-18m/p | H | Me | sBu |
| 3-19m/p | H | Me | tBu |
| 3-20m/p | H | Me | Pn |
| 3-21m/p | H | Me | Hx |
| 3-22m/p | H | Et | Me |
| 3-23m/p | H | Et | Et |
| 3-24m/p | H | Et | Pr |
| 3-25m/p | H | Et | iPr |
| 3-26m/p | H | Pr | Me |
| 3-27m/p | H | Pr | Et |
| 3-28m/p | H | Pr | Pr |
| 3-29m/p | H | Pr | iPr |
| 3-30m/p | H | iPr | Me |
| 3-31m/p | H | iPr | Et |
| 3-32m/p | H | iPr | Pr |
| 3-33m/p | H | iPr | iPr |
| 3-34m/p | H | Bu | Me |
| 3-35m/p | H | Bu | Et |
| 3-36m/p | H | Bu | Pr |

TABLE 3-continued

| Cpd. No. | R⁶ | R² | R⁴ |
|---|---|---|---|
| 3-37m/p | H | Bu | iPr |
| 3-38m/p | H | iBu | Me |
| 3-39m/p | H | iBu | Et |
| 3-40m/p | H | iBu | Pr |
| 3-41m/p | H | iBu | iPr |
| 3-42m/p | H | sBu | Me |
| 3-43m/p | H | sBu | Et |
| 3-44m/p | H | sBu | Pr |
| 3-45m/p | H | sBu | iPr |
| 3-46m/p | H | tBu | Me |
| 3-47m/p | H | tBu | Et |
| 3-48m/p | H | tBu | Pr |
| 3-49m/p | H | tBu | iPr |
| 3-50m/p | H | p-ClPh | H |
| 3-51m/p | H | p-ClPh | Me |
| 3-52m/p | H | p-ClPh | Et |
| 3-53m/p | H | p-ClPh | Pr |
| 3-54m/p | H | p-ClPh | iPr |
| 3-55m/p | H | p-ClPh | Bu |
| 3-56m/p | H | p-ClPh | iBu |
| 3-57m/p | H | p-ClPh | sBu |
| 3-58m/p | H | p-ClPh | tBu |
| 3-59m/p | H | p-ClPh | Pn |
| 3-60m/p | H | p-ClPh | Hx |
| 3-61m/p | H | m-ClPh | Me |
| 3-62m/p | H | m-ClPh | Et |
| 3-63m/p | H | m-ClPh | Pr |
| 3-64m/p | H | m-ClPh | iPr |
| 3-65m/p | H | p-FPh | Me |
| 3-66m/p | H | p-FPh | Et |
| 3-67m/p | H | p-FPh | Pr |
| 3-68m/p | H | p-FPh | iPr |
| 3-69m/p | H | p-MeOPh | Me |
| 3-70m/p | H | p-MeOPh | Et |
| 3-71m/p | H | p-MeOPh | Pr |
| 3-72m/p | H | p-MeOPh | iPr |
| 3-73m/p | H | m-MeOPh | Me |
| 3-74m/p | H | m-MeOPh | Et |
| 3-75m/p | H | m-MeOPh | Pr |
| 3-76m/p | H | m-MeOPh | iPr |
| 3-77m/p | H | 3,4-diMeoPh | Me |
| 3-78m/p | H | 3,4-diMeOPh | Et |
| 3-79m/p | H | 3,4-diMeOPh | Pr |
| 3-80m/p | H | 3,4-diMeOPh | iPr |
| 3-81m/p | H | p-HOPh | Me |
| 3-82m/p | H | p-HOPh | Et |
| 3-83m/p | H | p-HOPh | Pr |
| 3-84m/p | H | p-HOPh | iPr |
| 3-85m/p | H | p-NO₂Ph | Me |
| 3-86m/p | H | p-MeNHPh | Pr |
| 3-87m/p | Cl | H | H |
| 3-88m/p | Cl | H | Me |
| 3-89m/p | Cl | H | Et |
| 3-90m/p | Cl | H | Pr |
| 3-91m/p | Cl | H | iPr |
| 3-92m/p | Cl | H | Bu |
| 3-93m/p | Cl | H | iBu |
| 3-94m/p | Cl | H | sBu |
| 3-95m/p | Cl | H | Pn |
| 3-96m/p | Cl | H | Hx |
| 3-97m/p | Cl | Me | H |
| 3-98m/p | Cl | Me | Me |
| 3-99m/p | Cl | Me | Et |
| 3-100m/p | Cl | Me | Pr |
| 3-101m/p | Cl | Me | iPr |
| 3-102m/p | Cl | Me | Bu |
| 3-103m/p | Cl | Me | sBu |
| 3-104m/p | Cl | Me | tBu |
| 3-105m/p | Cl | Me | Pn |
| 3-106m/p | Cl | Me | Hx |
| 3-107m/p | Cl | Et | Me |
| 3-108m/p | Cl | Et | Et |
| 3-109m/p | Cl | Et | Pr |
| 3-110m/p | Cl | Et | iPr |
| 3-111m/p | Cl | Pr | Me |
| 3-112m/p | Cl | Pr | Et |

TABLE 3-continued

| Cpd. No. | $R^6$ | $R^2$ | $R^4$ |
|---|---|---|---|
| 3-113m/p | Cl | Pr | Pr |
| 3-114m/p | Cl | Pr | iPr |
| 3-115m/p | Cl | iPr | Me |
| 3-116m/p | Cl | iPr | Et |
| 3-117m/p | Cl | iPr | Pr |
| 3-118m/p | Cl | iPr | iPr |
| 3-119m/p | Cl | Bu | Me |
| 3-120m/p | Cl | Bu | Et |
| 3-121m/p | Cl | Bu | Pr |
| 3-122m/p | Cl | Bu | iPr |
| 3-123m/p | Cl | iBu | Me |
| 3-124m/p | Cl | iBu | Et |
| 3-125m/p | Cl | iBu | Pr |
| 3-126m/p | Cl | iBu | iPr |
| 3-127m/p | Cl | sBu | Me |
| 3-128m/p | Cl | sBu | Et |
| 3-129m/p | Cl | sBu | Pr |
| 3-130m/p | Cl | sBu | iPr |
| 3-131m/p | Cl | tBu | Me |
| 3-132m/p | Cl | tBu | Et |
| 3-133m/p | Cl | tBu | Pr |
| 3-134m/p | Cl | tBu | iPr |
| 3-135m/p | Cl | p-ClPh | Me |
| 3-136m/p | Cl | p-ClPh | Et |
| 3-137m/p | Cl | p-ClPh | Pr |
| 3-138m/p | Cl | p-ClPh | iPr |
| 3-139m/p | Cl | m-ClPh | Me |
| 3-140m/p | Cl | p-FPh | Me |
| 3-141m/p | Cl | p-FPh | Et |
| 3-142m/p | Cl | p-FPh | Pr |
| 3-143m/p | Cl | p-FPh | iPr |
| 3-144m/p | Cl | p-MeOPh | H |
| 3-145m/p | Cl | p-MeOPh | Me |
| 3-146m/p | Cl | p-MeOPh | Et |
| 3-147m/p | Cl | p-MeOPh | Pr |
| 3-148m/p | Cl | p-MeOPh | iPr |
| 3-149m/p | Cl | p-MeOPh | Bu |
| 3-150m/p | Cl | p-MeOPh | iBu |
| 3-151m/p | Cl | p-MeOPh | sBu |
| 3-152m/p | Cl | p-MeOPh | tBu |
| 3-153m/p | Cl | p-MeOPh | Pn |
| 3-154m/p | Cl | p-MeOPh | Hx |
| 3-155m/p | Cl | m-MeOPh | Me |
| 3-156m/p | Cl | m-MeOPh | Et |
| 3-157m/p | Cl | m-MeOPh | Pr |
| 3-158m/p | Cl | m-MeOPh | iPr |
| 3-159m/p | Cl | 3,4-diMeOPh | Me |
| 3-160m/p | Cl | 3,4-diMeOPh | Et |
| 3-161m/p | Cl | 3,4-diMeOPh | Pr |
| 3-162m/p | Cl | 3,4-diMeOPh | iPr |
| 3-163m/p | Cl | p-HOPh | Me |
| 3-164m/p | Cl | p-HOPh | Et |
| 3-165m/p | Cl | p-HOPh | Pr |
| 3-166m/p | Cl | p-HOPh | iPr |
| 3-167m/p | Cl | p-NO$_2$Ph | Me |
| 3-168m/p | Cl | p-MeNHPh | Me |
| 3-169m/p | Br | H | Me |
| 3-170m/p | Br | H | Et |
| 3-171m/p | Br | H | Pr |
| 3-172m/p | Br | H | iPr |
| 3-173m/p | Br | Me | Me |
| 3-174m/p | Br | Me | Et |
| 3-175m/p | Br | Me | Pr |
| 3-176m/p | Br | Me | iPr |
| 3-177m/p | Br | Et | Me |
| 3-178m/p | Br | Pr | Me |
| 3-179m/p | Br | iPr | Me |
| 3-180m/p | Br | Bu | Me |
| 3-181m/p | Br | iBu | Me |
| 3-182m/p | Br | sBu | Me |
| 3-183m/p | Br | tBu | Me |
| 3-184m/p | Br | p-ClPh | Me |
| 3-185m/p | Br | m-ClPh | Me |
| 3-186m/p | Br | p-FPh | Me |
| 3-187m/p | Br | p-FPh | Et |
| 3-188m/p | Br | p-FPh | Pr |
| 3-189m/p | Br | p-FPh | iPr |
| 3-190m/p | Br | p-MeOPh | Me |
| 3-191m/p | Br | m-MeOPh | Me |
| 3-192m/p | Br | 3,4-diMeOPh | Me |
| 3-193m/p | Br | p-HOPh | Me |
| 3-194m/p | Br | p-MeNHPh | Me |
| 3-195m/p | F | Me | Me |
| 3-196m/p | F | Me | Et |
| 3-197m/p | F | Me | Pr |
| 3-198m/p | F | Me | iPr |
| 3-199m/p | Me | H | Me |
| 3-200m/p | Me | H | Et |
| 3-201m/p | Me | H | Pr |
| 3-202m/p | Me | H | iPr |
| 3-203m/p | Me | Me | Me |
| 3-204m/p | Me | Me | Et |
| 3-205m/p | Me | Me | Pr |
| 3-206m/p | Me | Me | iPr |
| 3-207m/p | Me | p-ClPh | Me |
| 3-208m/p | Me | p-ClPh | Et |
| 3-209m/p | Me | p-ClPh | Pr |
| 3-210m/p | Me | p-ClPh | iPr |
| 3-211m/p | Me | p-MeOPh | Me |
| 3-212m/p | Me | p-MeOPh | Et |
| 3-213m/p | Me | p-MeOPh | Pr |
| 3-214m/p | Me | p-MeOPh | iPr |
| 3-215m/p | Et | H | Me |
| 3-216m/p | Et | Me | Me |
| 3-217m/p | Et | p-ClPh | Me |
| 3-218m/p | Et | p-MeOPh | Me |
| 3-219m/p | Pr | H | Me |
| 3-220m/p | Pr | Me | Me |
| 3-221m/p | Pr | p-ClPh | Me |
| 3-222m/p | Pr | p-MeOPh | Me |
| 3-223m/p | iPr | H | Me |
| 3-224m/p | iPr | Me | Me |
| 3-225m/p | iPr | p-ClPh | Me |
| 3-226m/p | iPr | p-MeOPh | Me |
| 3-227m/p | iPr | p-FPh | Me |
| 3-228m/p | Bu | H | Me |
| 3-229m/p | Bu | Me | Me |
| 3-230m/p | Bu | p-ClPh | Me |
| 3-231m/p | Bu | p-MeOPh | Me |
| 3-232m/p | Bu | p-HOPh | Me |
| 3-233m/p | iBu | H | Me |
| 3-234m/p | iBu | Me | Me |
| 3-235m/p | iBu | p-ClPh | Me |
| 3-236m/p | iBu | p-MeOPh | Me |
| 3-237m/p | iBu | p-FPh | Me |
| 3-238m/p | iBu | p-MeNHPh | Me |
| 3-239m/p | sBu | H | Me |
| 3-240m/p | sBu | Me | Me |
| 3-241m/p | sBu | Et | Me |
| 3-242m/p | sBu | p-MeOPh | Me |
| 3-243m/p | sBu | p-FPh | Me |
| 3-244m/p | tBu | H | Me |
| 3-245m/p | tBu | Me | Me |
| 3-246m/p | tBu | Et | Me |
| 3-247m/p | tBu | p-HOPh | Me |
| 3-248m/p | tBu | p-FPh | Me |
| 3-249m/p | tBu | p-MeOPh | Me |
| 3-250m/p | Pn | H | Me |
| 3-251m/p | Pn | Me | Me |
| 3-252m/p | Pn | p-ClPh | Me |
| 3-253m/p | Pn | m-ClPh | Me |
| 3-254m/p | Pn | p-MeOPh | Me |
| 3-255m/p | Pn | m-MeOPh | Me |
| 3-256m/p | Pn | 3,4-diMeOPh | Me |
| 3-257m/p | Pn | p-NO$_2$Ph | Me |
| 3-258m/p | Hx | H | Me |
| 3-259m/p | Hx | Me | Me |
| 3-260m/p | Hx | p-ClPh | Me |
| 3-261m/p | Hx | p-FPh | Me |
| 3-262m/p | Hx | p-MeOPh | Me |
| 3-263m/p | Hx | p-HOPh | Me |
| 3-264m/p | H | 2-Thi | Me |

TABLE 3-continued

| Cpd. No. | R⁶ | R² | R⁴ |
|---|---|---|---|
| 3-265m/p | Cl | 2-Thi | Me |
| 3-266m/p | H | 3-Pyr | Me |
| 3-267m/p | Cl | 3-Pyr | Me |
| 3-268m/p | H | 2-Fur | Me |
| 3-269m/p | Cl | 2-Fur | Me |

TABLE 4

| Cpd. No. | R² | R³ | R⁴ | R⁵ |
|---|---|---|---|---|
| 4-1 | H | Cl | H | H |
| 4-2 | Cl | H | H | H |
| 4-3 | H | H | Cl | H |
| 4-4 | H | H | H | Cl |
| 4-5 | Cl | Cl | H | H |
| 4-6 | Cl | H | Cl | H |
| 4-7 | Cl | H | H | Cl |
| 4-8 | H | Cl | Cl | H |
| 4-9 | H | Cl | H | Cl |
| 4-10 | H | H | Cl | Cl |
| 4-11 | Cl | Cl | Cl | H |
| 4-12 | Cl | Cl | H | Cl |
| 4-13 | Cl | H | Cl | Cl |
| 4-14 | H | Cl | Cl | Cl |
| 4-15 | Cl | Cl | Cl | Cl |
| 4-16 | H | Br | H | H |
| 4-17 | H | F | H | H |
| 4-18 | H | I | H | H |
| 4-19 | H | OH | H | H |
| 4-20 | H | OMe | H | H |
| 4-21 | H | OEt | H | H |
| 4-22 | H | OPr | H | H |
| 4-23 | H | OiPr | H | H |
| 4-24 | H | OBu | H | H |
| 4-25 | H | OiBu | H | H |
| 4-26 | H | OsBu | H | H |
| 4-27 | H | OtBu | H | H |
| 4-28 | H | Me | H | H |
| 4-29 | H | Et | H | H |
| 4-30 | H | Pr | H | H |
| 4-31 | H | iPr | H | H |
| 4-32 | H | Bu | H | H |
| 4-33 | H | iBu | H | H |
| 4-34 | H | sBu | H | H |
| 4-35 | H | tBu | H | H |
| 4-36 | H | NH₂ | H | H |
| 4-37 | H | NHMe | H | H |
| 4-38 | H | NHEt | H | H |
| 4-39 | H | NHPr | H | H |
| 4-40 | H | NHiPr | H | H |
| 4-41 | H | NHBu | H | H |
| 4-42 | H | NHiBu | H | H |
| 4-43 | H | NHsBu | H | H |
| 4-44 | H | NHtBu | H | H |
| 4-45 | H | CF₃ | H | H |
| 4-46 | H | Cl | Br | H |
| 4-47 | H | Cl | OMe | H |
| 4-48 | H | Cl | Me | H |
| 4-49 | H | Cl | NHMe | H |
| 4-50 | H | Cl | CF₃ | H |
| 4-51 | H | OMe | H | Me |
| 4-52 | H | OMe | H | NHMe |
| 4-53 | H | OMe | H | CF₃ |
| 4-54 | NHMe | Me | H | H |
| 4-55 | CF₃ | Me | H | H |
| 4-56 | H | NHMe | H | CF₃ |
| 4-57 | H | NHMe | H | OMe |
| 4-58 | OMe | Cl | Br | H |
| 4-59 | NHMe | Cl | Br | H |
| 4-60 | Me | Cl | Br | H |
| 4-61 | OMe | Cl | OMe | OMe |
| 4-62 | Me | Cl | NHMe | NHMe |

TABLE 4-continued

| Cpd. No. | R² | R³ | R⁴ | R⁵ |
|---|---|---|---|---|
| 4-63 | Cl | Cl | Me | Me |
| 4-64 | H | NMe₂ | H | H |
| 4-65 | H | NEt₂ | H | H |
| 4-66 | H | NO₂ | H | H |
| 4-67 | H | NHCOMe | H | H |
| 4-68 | H | NHCOEt | H | H |
| 4-69 | H | NHCOPr | H | H |
| 4-70 | H | NHCOBu | H | H |
| 4-71 | H | NMePr | H | H |

Of the compounds listed above, the following are preferred, that is to say Compounds No. 1-1, 1-2, 1-4, 1-6, 1-8, 1-10, 1-12, 1-14, 1-16, 1-18, 1-22, 1-24, 1-28, 1-32, 1-33, 1-34, 1-38, 1-39, 1-40, 1-56, 1-89, 1-90, 1-91, 1-144, 1-145, 1-147, 2-1, 2-2, 2-10, 2-11, 2-12, 2-13, 2-16, 2-17, 2-20, 2-21, 2-22, 2-29, 2-30, 2-32, 2-39, 2-40, 2-42, 2-44, 2-45, 2-97, 2-98, 2-99, 2-100, 2-101, 2-102, 2-103, 2-107, 3-2, 3-51, 3-87, 3-88, 3-144, 3-145, 3-169, 3-264, 3-265, 3-266, 3-267, 3-268 and 3-269, of which the more preferred compounds are Compounds No. 1-2, 2-1, 2-2, 2-10, 2-20, 2-21, 2-97, 2-98, 2-99, 2-100 and 2-107. The most preferred are Compounds No.:

2-1. 3-(3-Quinuclidinyloxy)isoxazole, including the

R-(+)-3-(3-quinuclidinyloxy)isoxazole and

S-(−)-3(3-quinuclidinyloxy)isoxazole isomers; isoxazole;

2-20. 4-Chloro-3-(3quinuclidinyloxy)isoxazole;

2-107. 4-Chloro-3-(3quinuclidinyloxy)-5-phenyl-isoxazole;

and pharmaceutically acceptable salts thereof, especially the hydrochlorides.

The compounds of the present invention can be prepared by a variety of methods well known for the preparation of compounds of this type. For example, in general terms, they may be prepared by the condensation of a compound of formula (II):

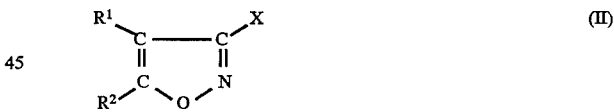

(II)

with a compound of formula (III):

(III)

(in the above formulae, $R^1$, $R^2$ and $R^3$ are as defined above and X and Y represent complementary leaving groups) under conditions to effect condensation.

For example, X may represent a halogen atom (e.g. a chlorine, bromine or iodine atom) and Y may represent a a hydroxy group or a group of formula MO—, where M represents a metal (e.g. alkali metal, especially sodium or potassium) atom, or X and Y may both represent hydroxy groups, in which case the reaction is carried out in the presence of a dehydrating agent. The compound may then, if desired, be salified to prepare a salt thereof.

In more detail, one preferred method of preparing the compounds of the present invention comprises reacting a compound of formula (IV):

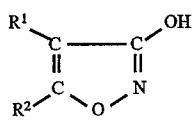 (IV)

(in which R¹ and R² are as defined above) with a compound of formula (V):

R³—OH        (V)

(in which R³ is as defined above) in the presence of a dehydrating agent, to give the compound of formula (I), and then, if desired, salifying the resulting compound of formula (I).

There is no particular restriction on the nature of the dehydrating agent employed in this reaction, and any compound capable of participating in a condensation reaction to remove the elements of water may be employed, as is well known in the art, provided that it does not have any adverse effect on the reagents. A particularly preferred dehydrating agent which may be employed in the present reaction is that compound prepared by reacting diethyl azodicarboxylate with triphenylphosphine, i.e.

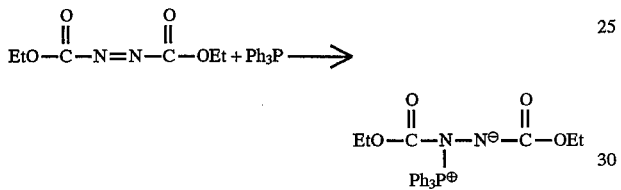

in which Ph represents a phenyl group and Et represents an ethyl group.

This reaction may be carried out using Mitsunobu's reaction, as described in Bull. Chem. Soc. Japan, 40, 2380 (1967).

Specifically, the reaction is preferably carried out in the presence of an organic solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene or toluene; ethers, such as dioxane or tetrahydrofuran; nitriles, such as acetonitrile; ketones, such as acetone or methyl ethyl ketone; amides, especially fatty acid amides, such as dimethylformamide or dimethylacetamide; and sulfoxides, such as dimethyl sulfoxide.

There is no particular restriction on the molar ratio of the two reagents, and approximately equimolar amounts or a slight excess of the compound of formula (V) are preferred.

The reaction can take place over a wide range of temperatures, and the precise reaction temperature is not critical to the invention. In general, we find it convenient to carry out the reaction at a temperature of from −20° C. to +50° C., and, in practice, room temperature is convenient and most preferred. The time required for the reaction may also vary widely, depending on many factors, notably the reaction temperature and the nature of the reagents. However, provided that the reaction is effected under the preferred conditions outlined above, a period of from 5 to 48 hours will usually suffice, a period of around 24 hours being generally suitable.

The product of this reaction may be separated from the reaction mixture by conventional means. For example, one suitable recovery procedure comprises extracting the mixture with a suitable organic solvent, such as ethyl acetate, removing the solvent from the extract, generally by evaporation, and then, if required, subjecting the product to a further purification step, for example by recrystallisation or by one of the chromatography techniques, such as column chromatography or preparative thin layer chromatography.

An alternative preferred method of preparing the compounds of the present invention, and particularly those wherein R¹ is as defined above and R² represents an optionally substituted phenyl group or a heterocyclic group, comprises reacting a halogen or sulfo derivative of either the isoxazole compound or the piperidyl or quinuclidinyl compound of formula (VI):

Rᵃ—X'        (VI)

with a hydroxy compound of formula (VII):

Rᵇ—OH        (VII)

or with a corresponding metal compound of formula (VIIa):

Rᵇ—OM        (VIIa)

where:

X' represents a halogen atom or a sulfo group; M represents a metal atom, preferably an alkali metal atom and most preferably a sodium or potassium atom; and one of Rᵃ and Rᵇ represents a group of formula (VIII):

 (VIII)

and the other of Rᵃ and Rᵇ represents a group R³, as defined above. A preferred reaction comprises reacting a compound of formula (IX):

 (IX)

(in which R¹, R² and X' are as defined above) with a hydroxy compound of formula (X):

HO—R³        (X)

or with a corresponding metal compound of formula (Xa):

MO—R³        (Xa)

(in which M and R³ are as defined above). In this reaction, X' is preferably a halogen atom, and most preferably a chlorine atom.

There is no particular restriction on the molar ratio of the two reagents, although, since the reaction requires equal amounts of each reagent, approximate molar equality is preferred. However, a molar excess of either component is possible, although, since any excess is merely wasted, any such excess is preferably minimised.

The reaction is normally and preferably carried out in the presence of a non-aqueous solvent. There is no particular restriction on the nature of the solvent to be employed, provided that it has no adverse effect on the reaction or on the reagents involved and that it can dissolve the reagents, at least to some extent. Examples of suitable solvents include: halogenated aliphatic hydrocarbons, such as methylene chloride, 1,2-dichloroethane, chloroform and carbon tetrachloride; ethers, such as diethyl ether, dibutyl ether, diisobutyl ether, dioxane, tetrahydrofuran and ethylene glycol dimethyl ether; aromatic hydrocarbons, such as benzene, toluene and xylene; esters, such as ethyl acetate; amides, such as dimethylformamide and hexamethylsulfonamide; and mixtures of any two or more of these solvents.

The reaction can take place over a wide range of temperatures, and the precise reaction temperature is not critical to the invention. In general, we find it convenient to carry out the reaction at a temperature of from 0° C. to 100° C., and in practice from 0° C. to 50° C. is more preferred. The time required for the reaction may also vary widely, depending on many factors, notably the reaction temperature and the nature of the reagents. However, provided that the reaction is effected under the preferred conditions outlined above, a period of from 1 to 48 hours will usually suffice, and in practice a period of from 1 to 20 hours is preferred.

After completion of the reaction, the desired compound may be separated from the reaction mixture by any suitable recovery procedure. For example, one suitable procedure comprises: pouring the reaction mixture into ice-water; extracting the mixture with a water-immiscible organic solvent, such as ethyl acetate; removing the solvent from the extract, e.g. by distillation; and then, if required, subjecting the product to a further purification step, for example by recrystallisation or by one of the chromatography techniques, such as column chromatograph or preparative thin layer chromatography.

The compound of formula (IX), which is used as one of the starting materials can be prepared, for example, as described in Chem. Ber., 100, 3326–3330 (1967) or by similar known methods.

The compounds of the present invention can exist in the form of various optical isomers and diastereomers because of the existence of asymmetric carbon atoms in the molecule. The optical isomers can be resolved using conventional techniques of optical resolution to give optically active compounds. The present invention covers both the individual isomers and mixtures (e.g. racemic mixtures) thereof, whether as obtained by their synthesis reaction or by mixing. If individual isomers are required, these may be prepared from mixtures, by conventional means, or they may be prepared by stereospecific synthesis techniques, as are well known in the art.

Salts of the compounds of formula (I) can be prepared by conventional salification techniques, well known to those skilled in the art. For example, the compound of formula (I) is dissolved in a suitable, preferably non-aqueous, solvent, and then the required acid, optionally also dissolved in a solvent, is added. The salt will generally precipitate (and the solvent or solvents are preferably so chosen that it does) and may be recovered by filtration or similar techniques. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as diethyl ether or tetrahydrofuran; and aromatic hydrocarbons, such as benzene or toluene. There is no restriction on the molar ratios of the compound of formula (I) to the acid, but about equimolar proportions or a slight excess of the acid are preferred, e.g. from 1 to 1.2 equivalents of acid per equivalent of the compound of formula (I). The reaction can take place over a wide range of temperatures, and the precise reaction temperature is not critical to the invention. In general, we find it convenient to carry out the reaction at a temperature of from −5° C. to 30° C.

The nature of the acid will, of course, depend on the salt which is to be prepared, but examples of suitable acids include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid or citric acid; and salts with amino acids, such as glutamic acid or aspartic acid.

After separation, the salt may, if required, be purified by recrystallisation from a suitable solvent, for example an alcohol, such as ethanol.

BIOLOGICAL ACTIVITY

As is demonstrated hereafter in the Experiments, the compounds of the present invention bind very specifically with the muscarinic receptors which are distributed in the brain among the receptors for acetylcholine, which is a neurotransmitter; in particular, they bind preferentially with the muscarinic 1 ($M_1$) receptors, which are located on the post-synaptic membrane. Moreover, they have anti-reserpine activity without anti-histamine activity, which is essential for use as an anti-depressant. Also they have antagonistic activity to $5-HT_3$ receptors. $5-HT_3$ antagonists are well known to have anti-anxiety and anti-psychotic activities. The compounds of the present invention can be expected to be useful for the treatment of associated symptoms of patients with cognitive disorders. As a result of this characteristic, the compounds of the present invention are expected to be useful for the therapy and prophylaxis of dementia of the Alzheimer type, senile dementia and Huntington's chorea, which are thought to be caused by injury to the acetylcholine biosynthesis pathway, with few side effects on the heart and intestinal tract.

In addition, because $5-HT_3$ antagonists are known to be useful as anti-emetic agents, and $M_1$ agonists are known to have shown centrally acting non-narcotic analgesic activity, the compounds of the present invention are predicted also to be useful as anti-emetic agents and as centrally acting non-narcotic analgesic agents.

We have also found that the compounds of the present invention have an ameliorating influence on ischemica-induced hyperviscosity of the blood, and this activity, too, can be expected to increase the cerebral microcirculation in patients with cognitive disorders, which will alleviate their symptoms.

Moreover, and most importantly, the compounds of the present invention have been found to have a low toxicity, The compounds of the present invention may therefore be used in the treatment and prophylaxis of disorders such as those referred to above, and, for this purpose, may be formulated as conventional pharmaceutical preparations, as is well known in the art. Thus, the compounds may be administered orally, e.g. in the form of tablets, capsules, granules, powders, syrups, or other such well known forms, or parenterally, e.g. by injections, suppositories, etc.

These pharmaceutical preparations can be prepared by conventional means and may contain known adjuvants of a type commonly used in this field, for example vehicles, binders, disintegrators, lubricants, correctives, etc. depending upon the intended use and form of the preparation. The does will depend upon the condition, age, and body weight of the patient as well as upon the nature and severity of the disorder to be treated, but in the case of oral administration to an adult human patient, we would normally suggest a total daily does of from 5 mg to 50 mg, which may be administered in a single dose or in divided doses, e.g. from one to three times a day.

The preparation of the compounds of the present invention is further illustrated by the following Examples, and the formulation of these compounds into pharmaceutically useful dosage forms is illustrated by the subsequent Formulations. The biological activities of the compounds are then illustrated by the subsequent Experiments.

EXAMPLE 1

4-Chloro-5-methyl-3-(3-quinuclidinyloxy)isoxazole

A solution of 7.86 g of triphenylphosphine in 100 ml of tetrahydrofuran was cooled to 5° C., and then 5.22 g of diethyl azodicarboxylate were added dropwise to the cooled solution, followed by 4.00 g of 4-chloro-3-hydroxy-5-methylisoxazole. 3.81 g of 3-hydroxyquinuclidine were then added to the resulting mixture, and the mixture was stirred at room temperature for 24 hours. At the end of this time, the solvent was removed from the mixture by distillation under reduced pressure. The resulting residue was purified by column chromatography through silica gel, using ethyl acetate as the eluent, to afford 4.72 g (yield 64.8%) of the title compound as a colorless powder, melting at 37°–38° C.

Infrared absorption spectrum (KBr) $v_{max}$ cm$^{-1}$: 1632, 1520, 1455.

Nuclear magnetic resonance spectrum (CDCl$_3$) δ ppm: 1.34–2.00 (4H, multiplet); 2.25–2.39 (1H, multiplet); 2.33 (3H, singlet); 2.68–3.04 (5H, multiplet); 3.26–3.35 (1H, multiplet); 4.71–4.78 (1H, multiplet).

EXAMPLE 2

3-(3-Quinuclidinyloxy)isoxazole

A solution of 9.18 g of triphenylphosphine in 100 ml of tetrahydrofuran was cooled to 5° C. 6.10 g of diethyl azodicarboxylate were then added dropwise to the cooled solution, after which 2.98 g of 3-hydroxyisoxazole and 4.45 g of 3-hydroxyquinuclidine were added, and the resulting mixture was stirred at room temperature for 24 hours. At the end of this time, the solvent was removed by distillation under reduced pressure, and the resulting residue was purified by column chromatography through silica gel, using ethyl acetate as the eluent, to afford 5.18 g (yield 76.2%) of the title compound as a colorless powder, melting at 80°–81° C.

Infrared absorption spectrum (KBr) $v_{max}$ cm$^{-1}$: 1581, 1486, 1465, 1423.

Nuclear magnetic resonance spectrum (CDCl$_3$) δ ppm: 1.27–1.97 (4H, multiplet); 2.24–2.30 (1H, multiplet); 2.68–3.01 (5H, multiplet); 4.69–4.76 (1H, multiplet); 5.96 (1H, doublet, J=1.97 Hz); 8.12 (1H, doublet, J=1.97 Hz).

EXAMPLE 3

4-Chloro-5-methyl-3-(3-quinuclidinyloxy)isoxazole hydrochloride

A solution of 2.30 g of 4-chloro-5-methyl-3-(3-quinuclidinyloxy)isoxazole (prepared as described in Example 1) in 30 ml of ethanol was cooled to 5° C. 2.50 ml of a 4N solution of hydrogen chloride in dioxane were then added dropwise to the solution. The resulting mixture was stirred at the same temperature for 10 minutes. At the end of this time, the reaction mixture was concentrated by evaporation under reduced pressure, and the solid residue thus obtained was recrystallized from isopropanol to afford 2.42 g (yield 91.6%) of the title compound as a colorless powder, melting at 195°–198° C. (with decomposition).

Infrared absorption spectrum (KBr) $v_{max}$ cm$^{-1}$: 1633, 1521, 1461, 1425.

Nuclear magnetic resonance spectrum (D$_2$O) δ ppm: 1.87–2.36 (4H, multiplet); 2.62–2.73 (1H, multiplet); 2.38 (3H, singlet); 3.28–3.57 (5H, multiplet); 3.75–3.84 (1H, multiplet); 5.09–5.15 (1H, multiplet).

EXAMPLE 4

A solution of 1.70 g of 3-(3-quinuclidinyloxy)isoxazole (prepared as described in Example 2) in 20 ml of ethanol was cooled to 5° C. 2.30 ml of a 4N solution of hydrogen chloride in dioxane were then added dropwise to the solution, and the resulting mixture was stirred at the same temperature for 10 minutes. At the end of this time, the reaction mixture was concentrated by distillation under reduced pressure, and the solid residue thus obtained was recrystallized from isopropanol to afford 1.83 g (yield 91.0%) of the title compound as a colorless powder, melting at 221°–223° C. (with decomposition).

Infrared absorption spectrum (KBr) $v_{max}$ cm$^{-1}$: 1579, 1475, 1456, 1430.

Nuclear magnetic resonance spectrum (D$_2$O) δ ppm: 1.16–2.35 (4H, multiplet); 2.64–2.70 (1H, multiplet); 3.28–3.53 (5H, multiplet); 3.75–3.84 (1H, multiplet); 5.05–5.11 (1H, multiplet); 6.24 (1H, doublet, J=1.97 Hz); 8.41 (1H, doublet, J=1.97 Hz).

EXAMPLE 5

R-(+)-3-(3-Quinuclidinyloxy)isoxazole

A solution of 62.50 g of 2,3-di-p-toluoyl-L-tartaric acid monohydrate in 200 ml of methanol was added to a solution of 30.00 g of 3-(3-quinuclidinyloxy)isoxazole (prepared as described in Example 2) in 800 ml of methanol, and the resulting mixture was allowed to stand overnight at room temperature. The crystals which precipitated were collected by filtration and washed with 300 ml of ethanol, to give 28.21 g (yield 62.8%) of crude crystals of 3-(3-R-quinuclidinyloxy)isoxazole 2,3-di-p-toluoyl-L-tartrate. A combination of these crude crystals and the ethanolic washings was used as the starting material for the synthesis described in Example 6.

Meanwhile, the crude crystals were recrystallized three times from methanol, to give 16.32 g of relatively pure 3-(3-R-quinclidinyloxy)isoxazole 2,3-di-p-toluoyl-L-tartrate as colorless columnar crystals, melting at 165°–166° C. (with decomposition) and having a refractive index $[\alpha]_D^{24}$=–48.7° (c=1.0, dimethylformamide).

16.00 g of the tartrate thus obtained were suspended in 200 ml of ethyl acetate, and the resulting solution was cooled to 5° C. 36 ml of 1N aqueous hydrochloric acid were added to the suspension, and the resulting mixture was stirred at the same temperature for 10 minutes. At the end of this time, the aqueous layer was separated and cooled to 5° C. 63 g of sodium carbonate were then added to it, and the mixture was extracted twice, each time with 200 ml of ethyl acetate. The organic layer then was dried over anhydrous magnesium sulfate, and the drying agent was removed by filtration. The solvent was then removed from the filtrate by distillation under reduced pressure. The resulting crystalline residue was crystallized from diisopropyl ether, to give 5.10 g (yield 34.0%) of the title compound, as colorless columnar crystals, melting at 69°–70° C.

$[\alpha]_D^{24}$=+7.7° (c=1.0, ethanol).

Infrared absorption spectrum (KBr) $\nu_{max}$ cm$^{-1}$: 1577, 1473, 1424.

Nuclear magnetic resonance spectrum (CDCl$_3$) δ ppm: 1.35–1.98 (4H, multiplet); 2.26–2.32 (1H, multiplet); 2.70–3.03 (5H, multiplet); 3.28–3.37 (1H, multiplet); 4.71–4.77 (1H, multiplet); 5.96 (1H, doublet, J=1.95 Hz); 8.12 (1H, doublet, J=1.95 Hz).

EXAMPLE 6

S-(–)-3-(3-Quinuclidinyloxy)isoxazole

A mixture of the filtrate and the washings obtained as described in Example 5 was concentrated by evaporation under reduced pressure, and the residue was suspended in 400 ml of ethyl acetate. The suspension was cooled to 5° C., and 353 ml of 1N aqueous hydrochloric acid were added to it; it was then stirred for a further 10 minutes. At the end of this time, the aqueous layer was separated and was cooled to 5° C.; 75.2 g of sodium carbonate were then added to it, and then the resulting mixture was extracted three times, each time with 400 ml of ethyl acetate. The combined extracts were dried over anhydrous magnesium sulfate, and then the drying agent was removed by filtration. The solvent was then removed from the filtrate by distillation under reduced pressure, to afford 20.01 g of 3-(3-quinuclidinyloxy) isoxazole, comprising mainly the S-isomer. The whole of this product was dissolved in 700 ml of methanol, and the resulting solution was mixed with a solution of 39.80 g of 2,3-di-p-toluoyl-D-tartaric acid in 200 ml of methanol. The resulting mixture was allowed to stand overnight at room temperature. The crystals which precipitated were collected by filtration and washed with 300 ml of ethanol. They were then recrystallized three times from methanol, to give 23.56 g (yield 52.7%) of 3-(3-S-quinuclidinyloxy)isoxazole di-p-toluoyl-D-tartrate, as colorless columnar crystals melting at 165°–166° C. (with decomposition) and having a specific rotation $[\alpha]_D^{24}$=+48.5° (c=1.0, dimethylformamide). 22.00 g of the tartrate thus obtained were suspended in 200 ml of ethyl acetate, and the suspension was cooled to 5° C. 50 ml of 1N aqueous hydrochloric acid were added to the suspension, and the resulting mixture was stirred at the same temperature for 10 minutes. At the end of this time, the aqueous layer was separated and cooled to 5° C., and then 10.59 g of sodium carbonate were added to it, and the mixture was extracted twice, each time with 200 ml of ethyl acetate. The organic layer was separated and dried over anhydrous magnesium sulfate, and then the drying agent was removed by filtration. The solvent was then removed from the filtrate by distillation under reduced pressure. The resulting crystalline residue was recrystallized from diisopropyl ether, to give 6.95 g (yield 46.3%) of the title compound, as colorless columnar crystals, melting at 69°–70° C.

$[\alpha]_D^{24}$=−7.6° (c=1.0, ethanol).

Infrared absorption spectrum (KBr) $\nu_{max}$ cm$^{-1}$: 1577, 1473, 1423.

Nuclear magnetic resonance spectrum (CDCl$_3$) δ ppm: 1.35–1.98 (4H, multiplet); 2.25–2.31 (1H, multiplet); 2.66–3.02 (5H, multiplet); 3.28–3.37 (1H, multiplet); 4.70–4.76 (1H, multiplet); 5.96 (1H, doublet, J=1.95 Hz); 8.12 (1H, doublet, J=1.95 Hz).

EXAMPLE 7

R-(–)-3-(3-Quinuclidinyloxy)isoxazole hydrochloride

A solution of 4.30 g of R-(+)-3-(3-quinuclidinyloxy)isoxazole (prepared as described in Example 5) in 50 ml of isopropanol was cooled to 5° C. and 6.07 ml of a 4N solution of hydrogen chloride in dioxane were added to it. The mixture was stirred for 10 minutes, and then the crystals which precipitated were collected by filtration and recrystallized from methanol, to give 4.85 g (yield 95.0%) of the title compound, as colorless needles, melting at 255°–257° C. (with decomposition).

$[\alpha]_D^{24}$=−29.7° (c=1.0, H$_2$O).

Infrared absorption spectrum (KBr) $\nu_{max}$ cm$^{-1}$: 1579, 1485, 1477, 1456, 1430.

Nuclear magnetic resonance spectrum (D$_2$O) δ ppm: 1.86–2.33 (4H, multiplet); 2.63–2.68 (1H, multiplet); 3.30–3.53 (5H, multiplet); 3.74–3.83 (1H, multiplet); 5.05–5.11 (1H, multiplet); 6.24 (1H, doublet, J=1.96 Hz); 8.41 (1H, doublet, J=1.96 Hz).

EXAMPLE 8

S-(+)-3-(3-Quinuclidinyloxy)isoxazole hydrochloride

A solution of 5.95 g of S-(–)-3-(3-quinuclidinyloxy)isoxazole (prepared as described in Example 6) in 60 ml of isopropanol was cooled to 5° C. and 8.41 ml of a 4N solution of hydrogen chloride in dioxane were added to it. The mixture was stirred for 10 minutes, and then the crystals which had precipitated were collected by filtration and recrystallized from ethanol, to give 6.64 g (yield 94.0%) of the title compound, as colorless needles, melting at 255°–257° C. (with decomposition).

$[\alpha]_D^{24}$=+29.8° (c=1.0, H$_2$O).

Infrared absorption spectrum (KBr) $\nu_{max}$ cm$^{-1}$: 1579, 1484, 1477, 1456, 1430.

Nuclear magnetic resonance spectrum (D$_2$O) δ ppm: 1.86–2.34 (4H, multiplet); 2.63–2.69 (1H, multiplet); 3.30–3.53 (5H, multiplet); 3.74–3.83 (1H, multiplet); 5.05–5.11 (1H, multiplet); 6.24 (1H, doublet, J=1.96 Hz); 8.41 (1H, doublet, J=1.96 Hz).

EXAMPLE 9

4-Chloro-3-(3-quinuclidinyloxy)-5-phenylisoxazole

A solution of 1.96 g of 3-quinuclidinol in 30 ml of dimethylformamide was cooled to 5° C. in an atmosphere of nitrogen. 0.67 g of sodium hydride (as a 55% w/w dispersion in mineral oil) was then added to the cooled solution, and then the solution was stirred at room temperature for 30 minutes. At the end of this time, the reaction mixture was cooled to 5° C., and 3.0 g of 3,4-dichloro-5-phenylisoxazole were added. The resulting mixture was then stirred at room temperature for 5 hours. At the end of this time, it was poured into 100 ml of ice-water and extracted twice, each time with 100 ml of ethyl acetate. The ethyl acetate extracts were combined and washed twice, each time with 100 ml of a 10% w/v aqueous solution of sodium chloride; they were then dried over anhydrous magnesium sulfate, after which the drying agent was removed by filtration. The solvent was then removed from the filtrate by distillation under reduced pressure. The residue thus obtained was purified by column chromatography through silica gel using a 10:1 by volume mixture of ethyl acetate and methanol as the eluent, to afford 4.21 g (yield 98.7%) of the title compound as a colorless and transparent oil.

$n_D^{28}=1.5701$

Infrared absorption spectrum (CHCl$_3$) $\nu_{max}$ cm$^{-1}$: 1625, 1520, 1460, 1375.

Nuclear magnetic resonance spectrum (CDCl$_3$) δ ppm: 1.38–2.05 (5H, multiplet); 2.31–3.40 (6H, multiplet); 4.80–4.86 (1H, multiplet); 7.44–7.54 (3H, multiplet); 7.93–7.99 (2H, multiplet).

EXAMPLE 10

4-Chloro-3-(3-quinuclidinyloxy)-5-phenylisoxazole hydrochloride

A solution of 2.12 g of 4-chloro-3-(3-quinuclidinyloxy)-5-phenylisoxazole (prepared as described in Example 9) in 20 ml of ethanol was cooled to 5° C. 2.1 ml of a 4N solution of hydrogen chloride in dioxane were then added dropwise to the solution, and the resulting mixture was stirred at room temperature for 30 minutes. At the end of this time, the reaction mixture was concentrated by distillation under reduced pressure and the solid residue thus obtained was recrystallized from ethanol to afford 2.35 g (yield 96.1%) of the title compound as a colorless powder, melting at 235°–237° C. (with decomposition).

Infrared absorption spectrum (KBr) $\nu_{max}$ cm$^{-1}$: 1627, 1522, 1450, 1421.

Nuclear magnetic resonance spectrum (hexadeuterated dimethyl sulfoxide) δ ppm: 1.81–2.56 (5H, multiplet); 3.16–3.79 (6H, multiplet); 5.08–5.14 (1H, multiplet); 7.59–7.65 (3H, multiplet); 7.90–7.95 (2H, multiplet).

EXAMPLE 11

5-Chloro-3-(1-methyl-4-piperidyloxy)-1,2-benzisoxazole

A solution of 1.53 g (13.3 mmole) of 4-hydroxy-1-methylpiperidine in 25 ml of dimethylformamide was cooled to 5° C. in an atmosphere of nitrogen. 0.58 g (13.3 mmole) of sodium hydride (as a 55% w/w dispersion in mineral oil) was added to the solution, and then the solution was stirred at room temperature for 30 minutes. The reaction mixture was cooled to 5° C., and then 2.50 g (13.3 mmole) of 3,5-dichloro-1,2-benzisoxazole were added to it; the resulting mixture was then stirred at 5° C. for 30 minutes and then at room temperature for 1 hour. At the end of this time, the mixture was poured into 50 ml of ice-water and then extracted twice, each time with 50 ml of ethyl acetate. The ethyl acetate layer was separated and washed with 100 ml of a 10% w/v aqueous solution of sodium chloride; it was then dried over anhydrous magnesium sulfate, and the drying agent was removed by filtration. The solvent was removed from the filtrate by distillation under reduced pressure. The resulting residue was purified by column chromatography through silica gel using ethyl acetate as the eluent to afford 2.38 g (yield 67.00%) of the title compound as a colorless powder, melting at 55°–56° C.

Infrared absorption spectrum (CHCl$_3$) cm$^{-1}$: 1535, 1470, 1440, 1360, 1310.

Nuclear magnetic resonance spectrum (CDCl$_3$) δ ppm: 1.73–3.00 (8H, multiplet); 2.32 (3H, singlet); 4.92 (1H, doubled doublet of doublets, J=13.5, 9.0 & 4.5 Hz); 7.30–7.76 (3H, multiplet).

EXAMPLE 12

5-Chloro-3-(1-methyl-4-piperidyloxy)-1,2-benzisoxazole hydrochloride

A solution of 2.20 g (8.24 mmole) of 5-chloro-3-(1-methyl-4-piperidyloxy)-1,2-benzisoxazole (prepared as described in Example 11) in 20 ml of ethanol was cooled to 5° C. 2.5 ml of a 4N solution of hydrogen chloride in dioxane were added dropwise to the cooled solution, and the resulting mixture was stirred at room temperature for 30 minutes. At the end of this time, the solvent was removed from the reaction mixture by distillation under reduced pressure. The solid residue thus obtained was recrystallized from ethanol to afford 2.47 g (yield 98.7%) of the title compound as colorless curd-like crystals, melting at 212°–214° C. (with decomposition).

Infrared absorption spectrum (KBr) $\nu_{max}$ cm$^{-1}$: 1532, 1471, 1440, 1311.

Nuclear magnetic resonance spectrum (hexadeuterated dimethyl sulfoxide) δ ppm: 2.06–2.43 (4H, multiplet); 2.78 (3H, singlet); 2.90–3.63 (4H, multiplet); 5.16 (1H, multiplet); 7.66–8.03 (3H, multiplet).

EXAMPLES 13 TO 108

Following procedures similar to those described in Examples 1 to 12, the following compounds were prepared.

EXAMPLE 13

(+)-4-Chloro-5-phenyl-3-(3-quinuclidinyloxy) isoxazole $n_D^{24}=1.6290$ $[\alpha]_D^{24}=+8.4°$ (c=1.0, CHCl$_3$).

EXAMPLE 14

(−)-4-Chloro-5-phenyl-3-(3-quinuclidinyloxy) isoxazole $n_D^{24}=1.6290$ $[\alpha]_D^{24}=-8.5°$ (c=1.0, CHCl$_3$).

EXAMPLE 15

(+)-4-Chloro-5-phenyl-3-(3-quinuclidinyloxy) isoxazole hydrochloride

Melting at 250°–255° C. (with decomposition)

$[\alpha]_D^{24}=+33.3°$ (c=1.0, H$_2$O).

EXAMPLE 16

(−)-4-Chloro-5-phenyl-3-(3-quinuclidinyloxy) isoxazole hydrochloride

Melting at 250°–255° C. (with decomposition)

$[\alpha]_D^{24}=-33.5°$ (c=1.0, H$_2$O).

EXAMPLE 17

5-Chloro-3-(4-piperidyloxy)-1,2-benzisoxazole hydrochloride

Melting at 253°–256° C. (with decomposition)

EXAMPLE 18

5-Methyl-3-(3-quinuclidinyloxy)isoxazole

Melting at 52°–53° C.

EXAMPLE 19

5-Methyl-3-(3-quinuclidinyloxy)isoxazole hydrochloride

Melting at 207°–209° C. (with decomposition).

EXAMPLE 20

5-Methyl-3-(4-piperidyloxy)isoxazole hydrochloride

Melting at 209°–211° C. (with decomposition)

EXAMPLE 21

5-(3-Pyridyl)-3-(3-quinuclidinyloxy)isoxazole hydrochloride

Melting at 250°–253° C. (with decomposition).

EXAMPLE 22

3-(1-Methyl-4-piperidyloxy)-5-(3-pyridyl)isoxazole hydrochloride

Melting at 217°–220° C. (with decomposition).

EXAMPLE 23

4-Chloro-3-(1-methyl-3-piperidyloxy)-5-phenylisoxazole $n_D^{28}$=1.5579.

EXAMPLE 24

4-Chloro-3-(1-methyl-4-piperidyloxy)-5-phenylisoxazole

Melting at 43°–44° C.

EXAMPLE 25

5-Phenyl-3-(3-quinuclidinyloxy)isoxazole $n_D^{28}$=1.5734.

EXAMPLE 26

3-(1-Methyl-3-piperidyloxy)-5-phenylisoxazole $n_D^{28}$=1.5612.

EXAMPLE 27

3-(1-Methyl-4-piperidyloxy)-5-phenylisoxazole

Melting at 70.5°–71.5° C.

EXAMPLE 28

5-(p-Chlorophenyl)-3-(3-quinuclidinyloxy)isoxazole

Melting at 81°–83° C.

EXAMPLE 29

5-(p-Chlorophenyl)-3-(1-methyl-3piperidyloxy)isoxazole $n_D^{28}$=1.5645.

EXAMPLE 30

5-(p-Chlorophenyl)-3-(1-methyl-4piperidyloxy)isoxazole

Melting at 122°–123° C.

EXAMPLE 31

4-Chloro-3-(1-methyl-3-piperidyloxy)-5-phenylisoxazole hydrochloride

Melting at 101°–102° C.

EXAMPLE 32

4-Chloro-3-(1-methyl-4-piperidyloxy)-5-phenylisoxazole hydrochloride

Melting at 192°–193° C. (with decomposition).

EXAMPLE 33

5-Phenyl-3-(3-quinuclidinyloxy)isoxazole hydrochloride

Melting at 238–240 (with decomposition).

EXAMPLE 34

(1-Methyl-3-piperidyloxy)-5-phenylisoxazole hydrochloride

Melting at 189°–190° C.

EXAMPLE 35

(1-Methyl-4-piperidyloxy)-5-phenylisoxazole hydrochloride

Melting at 210°–212° C. (with decomposition).

EXAMPLE 36

5-(p-Chlorophenyl)-3-(3-quinuclidinyloxy)isoxazole hydrochloride

Melting at 227°–229° C. (with decomposition).

EXAMPLE 37

5-(p-Chlorophenyl)-3-(1-methyl-3piperidyloxy) isoxazole hydrochloride

Melting at 215°–217° C. (with decomposition).

EXAMPLE 38

5-(p-Chlorophenyl)-3-(1-methyl-4piperidyloxy) isoxazole hydrochloride

Melting at 209°–211° C. (with decomposition).

EXAMPLE 39

4,5-Dimethyl-3-(3-quinuclidinyloxy)isoxazole $n_D^{26}$=1.5332

EXAMPLE 40

4,5-Dimethyl-3-(1-methyl-4-piperidyloxy)isoxazole $n_D^{26}$=1.5437

EXAMPLE 41

5-Ethyl-3-(3-quinuclidinyloxy)isoxazole

Melting at 71°–72° C.

EXAMPLE 42

5-Ethyl-3-(1-methyl-4-piperidyloxy)isoxazole $n_D^{26}$=1.5612

EXAMPLE 43

5-Isopropyl-3-(3-quinuclidinyloxy)isoxazole

Melting at 75°–76° C.

EXAMPLE 44

5-Isopropyl-3-(1-methyl-4-piperidyloxy)isoxazole $n_D^{24}$=1.5634

EXAMPLE 45

4-Chloro-5-ethyl-3-(1-methyl-4piperidyloxy) isoxazole

Melting at 78°–80° C.

EXAMPLE 46

4-Chloro-5-ethyl-3-(1-methyl-4piperidyloxy) isoxazole $n_D^{24}$=1.5802

EXAMPLE 47

4-Chloro-5-isopropyl-3-(3-quinuclidinyloxy) isoxazole

Melting at 81°–83° C.

EXAMPLE 48

4-Chloro-5-isopropyl-3-(1-methyl-4-piperidyloxy) isoxazole $n_D^{24}$=1.5724

EXAMPLE 49

5-Methyl-3-(1-methyl-4-piperidyloxy)isoxazole

Melting at 39°–40° C.

EXAMPLE 50

4-Chloro-5-methyl-3-(1-methyl-4-piperidyloxy) isoxazole

Melting at 30°–31° C.

EXAMPLE 51

3-(1-Methyl-4-piperidyloxy)isoxazole

Melting at 40°–40.5° C.

EXAMPLE 52

4-Chloro-3-(1-methyl-4-piperidyloxy)isoxazole $n_D^{26}$=1.6340

EXAMPLE 53

4-Fluoro-5-methyl-3-(3-quinuclidinyloxy)isoxazole

Melting at 40°–41° C.

EXAMPLE 54

4,5-Dimethyl-3-(3-quinuclidinyloxy)isoxazole hydrochloride

Melting at 212°–214° C. (with decomposition)

EXAMPLE 55

4,5-Dimethyl-3-(1-methyl-4-piperidyloxy)isoxazole hydrochloride

Melting at 219°–222° C. (with decomposition)

EXAMPLE 56

5-Ethyl-3-(3-quinuclidinyloxy)isoxazole hydrochloride

Melting at 211°–213° C. (with decomposition)

EXAMPLE 57

5-Ethyl-3-(1-methyl-4-piperidyloxy)isoxazole hydrochloride

Melting at 184°–186° C. (with decomposition)

EXAMPLE 58

5-Isopropyl-3-(3-quinuclidinyloxy)isoxazole hydrochloride

Melting at 210°–212° C. (with decomposition)

EXAMPLE 59

5-Isopropyl-3-(1-methyl-4-piperidyloxy)isoxazole hydrochloride

Melting at 196°–198° C. (with decomposition)

EXAMPLE 60

4-Chloro-5-ethyl-3-(3-quinuclidinyloxy)isoxazole hydrochloride

Melting at 219°–222° C. (with decomposition)

EXAMPLE 61

4-Chloro-5-ethyl-3-(1-methyl-4-piperidyloxy) isoxazole hydrochloride

Melting at 211°–214° C. (with decomposition)

EXAMPLE 62

4-Chloro-5-isopropyl-3-(3-quinuclidinyloxy) isoxazole

Melting at 213°–216° C. (with decomposition)

EXAMPLE 63

4-Chloro-5-isopropyl-3-(1-methyl-4-piperidyloxy) isoxazole

Melting at 209°–212° C. (with decomposition)

EXAMPLE 64

5-Methyl-3-(1-methyl-4-piperidyloxy)isoxazole hydrochloride

Melting at 198°–200° C. (with decomposition)

EXAMPLE 65

4-Chloro-5-methyl-3-(1-methyl-4-piperidyloxy) isoxazole hydrochloride

Melting at 211°–214° C. (with decomposition)

EXAMPLE 66

3-(1-Methyl-4-piperidyloxy)isoxazole fumarate

Melting at 148°–150° C. (with decomposition)

EXAMPLE 67

4-Chloro-3-(1-methyl-4-piperidyloxy)isoxazole hydrochloride

Melting at 201°–204° C. (with decomposition)

EXAMPLE 68

4-Fluoro-5-methyl-3-(3-quinuclidinyloxy)isoxazole hydrochloride

Melting at 200°–203° C. (with decomposition)

EXAMPLE 69

3-(1-Methyl-4-piperidyloxy)-1,2-benzisoxazole

Melting at 67°–68° C.

EXAMPLE 70

6-Chloro-3-(3-quinuclidinyloxy)-1,2-benzisoxazole

Melting at 73.5°–74.5° C.

EXAMPLE 71

6-Chloro-3-(1-methyl-3-piperidyloxy)-1,2-benzisoxazole

Melting at 64°–65° C.

EXAMPLE 72

6-Chloro-3-(1-methyl-4-piperidyloxy)-1,2-benzisoxazole

Melting at 106°–107.5° C.

EXAMPLE 73

7-Chloro-3-(3-quinuclidinyloxy)-1,2-benzisoxazole

Melting at 63°–64° C.

EXAMPLE 74

7-Chloro-3-(1-methyl-4-piperidyloxy)-1,2-benzisoxazole

Melting at 74°–75° C.

EXAMPLE 75

5-Methoxy-3-(3-quinuclidinyloxy)-1,2-benzisoxazole

Melting at 85°–86° C.

EXAMPLE 76

5-Methoxy-3-(1-methyl-4-piperidyloxy)-1,2-benzisoxazole $n_D^{26}$=1.5390

EXAMPLE 77

5-Fluoro-3-(3-quinuclidinyloxy)-1,2-benzisoxazole

Melting at 90°–91° C.

EXAMPLE 78

5-Fluoro-3-(1-methyl-4-piperidyloxy)-1,2-benzisoxazole

Melting at 83°–84° C.

EXAMPLE 79

5-Chloro-3-(1-ethyl-4-piperidyloxy)-1,2-benzisoxazole

Melting at 62°–63° C.

EXAMPLE 80

5-Chloro-3-(1-propyl-4-piperidyloxy)-1,2-benzisoxazole

Melting at 71°–72° C.

EXAMPLE 81

5-Chloro-3-(1-isobutyl-4-piperidyloxy)-1,2-benzisoxazole

Melting at 76°–77° C.

EXAMPLE 82

5-Methyl-3-(3-quinuclidinyloxy)-1,2-benzisoxazole

Melting at 94°–95° C.

EXAMPLE 83

5-Methyl-3-(1-methyl-4-piperidyloxy)-1,2-benzisoxazole

Melting at 87°–88° C.

EXAMPLE 84

5-Chloro-3-(1-methyl-3-piperidyloxy)-1,2-benzisoxazole

Melting at 61°–62° C.

EXAMPLE 85

5-Chloro-3-(3-quinuclidinyloxy)-1,2-benzisoxazole

Melting at 69°–70° C.

EXAMPLE 86

5-Chloro-3-(4-piperidyloxy)-1,2-benzisoxazole

Melting at 81°–82° C.

EXAMPLE 87

3-(1-Methyl-4-piperidyloxy)-1,2-benzisoxazole hydrochloride

Melting at 197°–199° C. (with decomposition)

EXAMPLE 88

6-Chloro-3-(3-quinuclidinyloxy)-1,2-benzisoxazole hydrochloride

Melting at 237°–239° C. (with decomposition)

EXAMPLE 89

6-Chloro-3-(1-methyl-3-piperidyloxy)-1,2-benzisoxazole hydrochloride

Melting at 213°–215° C. (with decomposition)

EXAMPLE 90

6-Chloro-3-(1-methyl-4-piperidyloxy)-1,2-benzisoxazole hydrochloride

Melting at 238°–240° C. (with decomposition)

EXAMPLE 91

7-Chloro-3-(3-quinuclidinyloxy)-1,2-benzisoxazole hydrochloride

Melting at 251°–253° C. (with decomposition)

EXAMPLE 92

7-Chloro-3-(1-methyl-4-piperidyloxy)-1,2-benzisoxazole hydrochloride

Melting at 238°–240° C. (with decomposition)

EXAMPLE 93

5-Methoxy-3-(3-quinuclidinyloxy)-1,2-benzisoxazole hydrochloride

Melting at 245°–247° C. (with decomposition)

EXAMPLE 94

5-Methoxy-3-(1-methyl-4-piperidyloxy)-1,2-benzisoxazole hydrochloride

Melting at 225°–227° C. (with decomposition)

EXAMPLE 95

5-Fluoro-3-(3-quinuclidinyloxy)-1,2-benzisoxazole hydrochloride

Melting at 231°–233° C. (with decomposition)

EXAMPLE 96

5-Fluoro-3-(1-methyl-4-piperidyloxy)-1,2-benzisoxazole hydrochloride

Melting at 234°–236° C. (with decomposition)

EXAMPLE 97

5-Chloro-3-(1-ethyl-4-piperidyloxy)-1,2-benzisoxazole hydrochloride

Melting at 186°–188° C. (with decomposition)

EXAMPLE 98

5-Chloro-3-(1-propyl-4-piperidyloxy)-1,2-benzisoxazole hydrochloride

Melting at 226°–228° C. (with decomposition)

EXAMPLE 99

5-Chloro-3-(1-isobutyl-4-piperidyloxy)-1,2-benzisoxazole hydrochloride

Melting at 215°–217° C. (with decomposition)

EXAMPLE 100

5-Methyl-3-(3-quinuclidinyloxy)-1,2-benzisoxazole hydrochloride

Melting at 262°–264° C. (with decomposition)

EXAMPLE 101

5-Methyl-3-(1-methyl-4-piperidyloxy)-1,2-benzisoxazole hydrochloride

Melting at 233°–235° C. (with decomposition)

EXAMPLE 102

5-Chloro-3-(1-methyl-3-piperidyloxy)-1,2-benzisoxazole hydrochloride

Melting at 204°–206° C. (with decomposition)

EXAMPLE 103

5-Chloro-3-(3-quinuclidinyloxy)-1,2-benzisoxazole hydrochloride

Melting at 269°–271° C. (with decomposition)

EXAMPLE 104

3-(1-Methyl-3-(1-piperidyloxy)-1,2-benzisoxazole hydrochloride

Melting at 188°–190° C. (with decomposition)

EXAMPLE 105

3-(3-Quinuclidinyloxy)-1,2-benzisoxazole hydrochloride

Melting at 248°–250° C. (with decomposition)

EXAMPLE 106

4-Chloro-5-phenyl-3-(3-piperidyloxy)isoxazole hydrochloride

Melting at 111°–113° C.

EXAMPLE 107

3-(3-Quinuclidinyloxy)-5-(2-thienyl)isoxazole hydrochloride

Melting at 240°–242° C. (with decomposition)

EXAMPLE 108

3-(1-Methylpiperidyloxy)-5-(2-thienyl)isoxazole hydrochloride

Melting at 216°–218° C. (with decomposition)

EXAMPLE 109

4-Chloro-3-(3-quinuclidinyloxy)isoxazole 6.99 g of (40.2 mmole) of diethyl diazodicarboxylate were added dropwise to a solution of 10.54 g (40.2 mmole) of triphenylphosphine in 150 ml of tetrahydrofuran, whilst cooling to 0°–10° C., and the resulting mixture was stirred at the same temperature for 30 minutes. At the end of this time, 5.10 g (40.2 mmole) of 3-quinuclidinol were added, and the mixture was stirred at 0°–5° C. for 30 minutes and then at room temperature for 24 hours. At the end of this time, the solvent was removed by distillation under reduced pressure, and the resulting residue was further purified by column chromatography through silica gel, using ethyl acetate as the eluent, to give 3.90 g (yield 50.9%) of the title compound as a colorless powder, melting at 68°–69° C.

Elemental analysis: Calculated for $C_{10}H_{13}N_2O_2Cl$: C, 52.52%; H, 5.73%; N, 12.25%; Cl, 15.51%. Found: C, 52.28%; H, 5.61%; N, 12.21%; Cl, 15.49%.

Infrared Absorption Spectrum (KBr), $v_{max}$ cm$^{-1}$: 1582, 1514, 1418.

Nuclear Magnetic Resonance Spectrum (CDCl$_3$, 270 MHz), δ ppm: 1.36–2.00 (4H, multiplet); 2.27–2.33 (1H, multiplet); 2.68–3.05 (5H, multiplet); 3.27–3.36 (1H, multiplet); 4.74–4.80 (1H, multiplet); 8.18 (1H, singlet).

EXAMPLE 110

4-Chloro-3-(3-quinuclidinyloxy)isoxazole hydrochloride 3.00 ml (12.0 mmole) of a 4N solution of hydrogen chloride in dioxane were added dropwise to a solution of 2.29 g (10.0 mmole) of 4-chloro-3-(3-quinuclidinyloxy) isoxazole (prepared as described in Example 109) in 20 ml of ethanol, whilst cooling at 5° C.; the mixture was then stirred at the same temperature for 10 minutes. At the end of this time, the solvent was removed by distillation under reduced pressure, and the solid residue was recrystallized from isopropanol, to give 2.40 g (yield 90.4%) of the title compound as a colorless powder, melting at 235°–238° C. (with decomposition).

Elemental analysis: Calculated for $C_{10}H_{14}N_2O_2Cl_2$: C, 45.30%; H, 5.32%; N, 10.57%; Cl, 26.74%. Found: C, 44.55%; H, 5.37%; N, 10.44%; Cl, 26.45%.

Infrared Absorption Spectrum (KBr), $\nu_{max}$ cm$^{-1}$: 1590, 1513, 1484, 1455, 1422.

Nuclear Magnetic Resonance Spectrum (CDCl$_3$, 270 MHz), δ ppm: 1.87–2.39 (4H, multiplet); 2.68–2.75 (1H, multiplet, J=0.97 Hz); 3.28–3.58 (5H, multiplet); 3.76–3.86 (1H, multiplet); 5.13–5.19 (1H, multiplet); 8.56 (1H, singlet).

FORMULATION 1

Capsules

| | |
|---|---|
| 5-Chloro-3-(1-Methyl-4-piperidyloxy)-1,2-benzisoxazole hydrochloride | 10.0 mg |
| Lactose | 153.6 mg |
| Corn starch | 100.0 mg |
| Magnesium stearate | 1.4 mg |
| Total | 280.0 mg |

Powders of the above compounds were mixed and passed through a 60 mesh sieve (Tyler standard), and 280 mg of the resulting powder was packed into a No. 3 gelatin capsule.

FORMULATION 2

Powders

The powder prepared as described in Formulation 1 was compressed to make tablets each containing 120 mg using a conventional tabletting machine.

FORMULATION 3

Capsules

| | |
|---|---|
| 3-(3-Quinuclidinyloxy)isoxazole hydrochloride | 10.0 mg |
| Lactose | 153.6 mg |
| Corn starch | 100.0 mg |
| Magnesium stearate | 1.4 mg |
| Total | 280.0 mg |

Powders of the above compounds were mixed and passed through a 60 mesh sieve (Tyler standard), and 280 mg of the resulting powder was packed into a No. 3 gelatin capsule.

FORMULATION 4

Powders

The powder prepared as described in Formulation 3 was compressed to make tablets each containing 120 mg using a conventional tabletting machine.

EXPERIMENT 1

Muscarinic receptor binding test

A membranous fraction prepared from the cerebral cortex of rats was added to the compound under test together with $^3$H-oxotremorine-M (to a final concentration of 3 nM), and the mixture was allowed to react at 30° C. for 60 minutes. At the end of this time, the mixture was filtered through a filter paper. The $^3$H radioactivity bound to the membrane which remained on the filter paper was determined by a liquid scintillation counter.

Since a compound which binds to muscarinic receptors will do so in place of the $^3$H-oxotremorine-M, a greater muscarinic binding activity of the test compound will be shown by a lower radioactivity in the membrane remaining on the filter paper. The concentration of the compound under test which lowers the $^3$H radioactivity by 50% (IC$_{50}$) is taken as an index of the muscarinic receptor binding ability of the test compound and is reported in Table 5 hereafter.

Test for selective binding to M$_1$ receptors

A membranous fraction prepared from the cerebral cortex of rats (where M$_1$ receptors are plentiful) was added to the compound under test together with $^3$H-pirenzepine (to a final concentration of 1 nM), and the mixture was allowed to react at 30° C. for 60 minutes. Meanwhile, a membranous fraction prepared from the heart of rats (where M$_2$ receptors predominate) was added to the compound under test together with $^3$H-quinuclidinyl benzylate (which combines non-selectively with both M$_1$ and M$_2$ receptors, to a final concentration of 0.12 nM), and the mixture was allowed to react at 30° C. for 120 minutes. In each case, at the end of the reaction period, the preparation was filtered and the radioactivity remaining on the filter paper was determined in a similar manner to that described above.

The results are also summarised in Table 5, below.

The compounds tested are identified in Table 5 by the following codes:

A1: 5-chloro-3-(1-methyl-4-piperidyloxy)-1,2-benzisoxazole hydrochloride (a compound of the invention, prepared as described in Example 12);

B1: Oxotremorine, a known M$_1$ agonist, which has the formula:

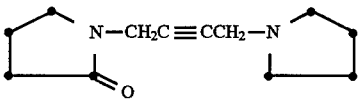

B2: RS-86, which has the formula:

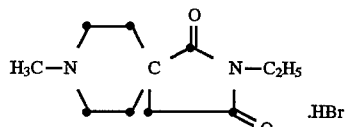

B3: AF-102-B, which has the formula:

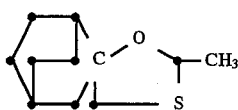

B4: Arecoline, which has the formula:

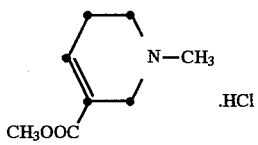

TABLE 5

| | (IC$_{50}$) | | | |
|---|---|---|---|---|
| Cpd. No. | Oxo-M (cerebral cortex) | Pirenzp (a) (cerebral cortex) | M$_1$ QNB (b) (heart) | selectivity (b)/(a) |
| A1 | 2.2 | 1.9 | 41 | 22 |
| B1 | 0.02 | 1.3 | 1.2 | 0.9 |
| B2 | 0.3 | 3.1 | 21 | 6.8 |
| B3 | 0.4 | 3.6 | 14 | 3.9 |
| B4 | 0.1 | 7.2 | 12 | 1.7 |

In the Table, Oxo-M is $^3$H-oxotremorine, Pirenzp is $^3$H-pirenzepine and QNB is $^3$H-quinuclidinyl benzylate.

EXPERIMENT 2

Anti-reserpine effect

It is considered that the sedation caused by the administration of reserpine or tetrabenazine to mice or rats produces an effect similar to the symptoms of clinical depression. Of the various pharmacological effects caused by these compounds, ptosis (drooping of the upper eyelid) and a reduction in body temperature have been widely used as indices of their activity, and it has been shown that any compound which inhibits either ptosis or lowering of the body temperature will also be active against the symptoms of clinical depression. Therefore, anti-reserpine or anti-tetrabenazine effects have been widely used for a long time as a method of screening for antidepressants. The test index used for the evaluation of the compounds of the present invention is the antagonistic effect of a test compound against reserpine-induced ptosis in mice.

The test animals employed were mature male mice of the ddY strain, 4 weeks old and each weighing 22 to 27 g. The animals were divided into groups, each including 3 mice. The compound under test was dissolved or suspended in an appropriate solvent [either physiological saline or a 0.5% CMC (carboxymethyl cellulose) solution] and administered orally to the mice of the test groups in the dose specified in the following Table 6. The mice in a control group were given only the solvent without any active compound, administered in a similar way. Immediately after administration, 2 mg/kg of reserpine were administered subcutaneously to every mouse. After 90 minutes, it was determined how much the eyelids had closed (degree of ptosis) by bringing the mouse out of its cage and observing the shape of the eye. For assessment of the results, normal mice without ptosis and, hence, with a normal circular eye were scored as 0, while a mouse which exhibited ptosis by ⅓ to ½ was scored as 1, a mouse which exhibited ptosis by ⅔ to slightly opened eyes was scored as 2, and a mouse with completely closed eyelids was scored as 3.

The results are shown in Table 6.

The labels of the bottles containing the sample solutions to be tested were all indicated by codes unknown to those responsible for administration, and the administration was carried out in a random order so that the scorers did not know which drug was administered to which mouse. From the scores obtained, the inhibition rate at each dose level was calculated from the following equation:

$$\text{Inhibition rate } (\%) = \left(1 - \frac{\text{Total score of the sample group}}{\text{Total score of the control group}}\right) \times 100$$

In assessing the results, inhibition rates not less than 71%, from 41% to 70%, and not more than 40% were considered to be (+), (±) and (−), respectively.

The test compounds employed are identified by the following codes:

A2: 4-Chloro-5-methyl-3-(3-quinuclidinyloxy)isoxazole hydrochloride (prepared as described in Example 3);

A3: 3-(3-Quinuclidinyloxy)isoxazole hydrochloride (prepared as described in Example 4);

A4: 5-Methyl-3-(3-quinuclidinyloxy)isoxazole hydrochloride (prepared as described in Example 19).

TABLE 6

Antagonistic effect against reserpine-induced ptosis

| Compound | Dose (mg/kg) | Administration route | Maximum inhibition rate (%) | Assessment |
|---|---|---|---|---|
| A2 | 3 | po | 60 | − |
| A2 | 30 | po | 100 | + |
| A3 | 1 | po | 21 | − |
| A3 | 3 | po | 57 | ± |
| A3 | 10 | po | 86 | + |
| A3 | 30 | po | 100 | + |
| A4 | 30 | po | 45 | ± |
| A4 | 100 | po | 80 | + |

EXPERIMENT 3

Inhibition of blood viscosity increase resulting from cerebral ischemia

The test animals used were adult male rats of the Wistar strain. Each rat was administered orally either a solution of 3-(3-quinuclidinyloxy)isoxazole hydrochloride (the compound prepared as described in Example 4) in suspension in a 0.5% CMC vehicle or the vehicle itself. Immediately after administration, 40 mg/kg of pentobarbital was administered intraperitoneally for anesthesia. The rat was fixed at the dorsal position, and 0.6 ml of a blood sample was taken from the common jugular vein on one side. The viscosity of each sample was measured using a viscometer (Biorheolyzer, a trade name for product of Tokyo Keiki) at shear values of 37.5/sec, 75/sec, 150/sec and 375/sec. 0.5 ml of blood was then taken from the other side and its viscosity was measured in the same way.

After the first two samples had been taken, the carotid arteries on both sides of each animal were ligated. One hour after ligation, in the case of the control animals (administered only the vehicle), the blood viscosity values had increased by between 5 and 20% at every shear rate (the slower the shear rate, the higher the viscosity). However, in the case of the animals to which the compound of the invention had been administered, the increase was significantly inhibited at every shear rate.

Accordingly, the compounds exhibit the ability to improve blood viscosity and can, therefore, be expected to improve microcirculation in cases of stroke.

EXPERIMENT 4

5-HT$_3$ receptor binding study

A membranous fraction prepared from the cerebral cortex of rats was incubated with the test compound and with $^3$H-GR65630 (to a final concentration of 1 nM, as a ligand to the 5-HT$_3$ receptors) at 37° C. for 45 minutes. At the end of this time, the samples were filtered. The $^3$H radioactivity bound to the filter paper was determined by a scintillation counter as in Experiment 1. Non-specific binding was determined by ondansetron ($10^{-5}$M). The results are summarised in Table 7, from which it can be seen that the compounds of the present invention bind to 5-HT$_3$ receptors as potently as ondansetron.

The test compounds employed are identified by the following codes:

A5: 4-Chloro-3-(3-quinuclidinyloxy)-5-phenylisoxazole hydrochloride (prepared as described in Example 10);

A6: 5-Chloro-3-(3-quinuclidinyloxy)-1,2-benzisoxazole (the compound prepared as described in Example 85);

A7: 5-(p-Chlorophenyl)-3-(3-quinuclidinyloxy)isoxazole hydrochloride (the hydrochloride of the compound prepared as described in Example 28);

A8: 4-Chloro-5-phenyl-3-(3-piperidyloxy)isoxazole hydrochloride (prepared as described in Example 106);

A9: 3-(3-Quinuclidinyloxy)-5-(2-thienyl)isoxazole hydrochloride (prepared as described in Example 107);

B5: Ondansetron.

TABLE 7

| Compound | IC$_{50}$ (×$10^{-7}$ M) |
|---|---|
| A5 | 2.2 |
| A6 | 1.8 |
| A7 | 3.2 |
| A8 | 2.6 |
| A9 | 1.5 |
| B5 | 2.4 |

EXPERIMENT 5

Effects upon the isolated guinea pig ileum

The ileum isolated from a guinea pig was hung in a Magnus cup filled with Tyrode's solution. The contractile force exerted by the ileum on the application of a selective 5-HT$_3$ agonist, 2-methyl-5-HT, was determined using an isometric transducer. A test compound was then added to the bath and the contractile force was again measured 30 minutes after the addition. The inhibition rate on the contractile force was calculated. The results are summarised in Table 8, from which it can be seen that the compound of the invention, 4-chloro-3-(3-quinuclidinyloxy)-5-phenylisoxazole hydrochloride (compound A5) was as potent an antagonist as ondansetron.

TABLE 8

| Compound | Concentration (M) | Inhibition (%) |
|---|---|---|
| A5 | $10^{-6}$ | 82 |
| B5 | $10^{-6}$ | 79 |

EXPERIMENT 6

Acute toxicity

Each of the compounds of Examples 3 and 4 was suspended in a 0.5% CMC solution, and the suspension was administered to mice in an amount sufficient to provide a dose of active compound of 75 mg/kg. The mice were observed for 5 days, during which time no deaths were observed, nor did the mice exhibit any adverse symptoms.

We claim:

1. A method for the treatment or prophylaxis of anxiety, depression or psychosis in a mammal, comprising administering to said mammal a pharmaceutically effective amount of at least one active compound, wherein the active compound is selected from the group consisting of a compound of the following formula (I) and pharmaceutically acceptable salts thereof:

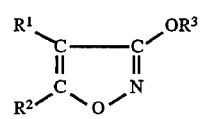

in which:

R$^1$ represents
a hydrogen atom,
a halogen atom or
an alkyl group having from 1 to 6 carbon atoms;

R$^2$ represents
a hydrogen atom,
an alkyl group having from 1 to 6 carbon atoms,
a phenyl group which is unsubstituted or which is substituted by at least one of substituent selected from the group consisting of
halogen atoms,
alkyl groups having from 1 to 6 carbon atoms,
alkoxy groups having from 1 to 6 carbon atoms,
alkylamino groups having from 1 to 4 carbon atoms,
dialkylamino groups in which each alkyl group has from 1 to 4 carbon atoms,
hydroxy groups,
nitro groups and
amino groups, or
a heterocyclic group selected from the group consisting of furyl, thienyl, pyrrolyl, pyridyl, thiazolyl, isothiazolyl, oxazolyl, isoxazolyl, imidazolyl, pyrazolyl, pyranyl, tetrahydrofuranyl, tetrahydrothienyl, pyrrolidinyl, thiazolidinyl, imidazolidinyl, imidazolinyl, oxazolinyl, oxazolidinyl, pyrazolidinyl, pyrrolidonyl, piperidonyl, oxazolidinyl, pyrazolidinyl, pyrrolidonyl, piperidonyl, pyridonyl, 2H-pyrrolyl, furazanyl and pyrazolinyl, said heterocyclic group being unsubstituted or being substituted by at least one substituent selected from the group consisting of
halogen atoms,
alkyl groups having from 1 to 6 carbon atoms,
alkoxy groups having from 1 to 6 carbon atoms,
alkylamino groups having from 1 to 4 carbon atoms,
dialkylamino groups in which each alkyl group has from 1 to 4 carbon atoms,
hydroxy groups, nitro groups and
amino groups; or $R^1$ and $R^2$ together form a group of formula $-CR^4=CR^5-CR^6=CR^7-$, in which $R^4$, $R^5$, $R^6$ and $R^7$ are independently selected from the group consisting of a hydrogen atom,
halogen atoms,
alkyl groups having from 1 to 6 carbon atoms,
alkoxy groups having from 1 to 4 carbon atoms,
halomethyl groups,
alkylamino groups having from 1 to 4 carbon atoms,
dialkylamino groups in which each alkyl group has from 1 to 4 carbon atoms,
hydroxy groups,
nitro groups,
aliphatic carboxylic acylamino groups having from 2 to 4 carbon atoms and
amino groups; and $R^3$ represents a quinuclidinyl group.

2. The method of claim 1, wherein $R^1$ represents a hydrogen atom, a halogen atom or an alkyl group having from 1 to 3 carbon atoms.

3. The method of claim 1, wherein $R^2$ represents a hydrogen atom; an alkyl group having from 1 to 3 carbon atoms; a phenyl group which is unsubstituted or which is substituted by at least one of substituents (a'), defined below; or said heterocyclic group being unsubstituted or being substituted by at least one of substituents (a'), defined below;

substituents (a'):
halogen atoms; alkyl groups having from 1 to 4 carbon atoms; alkoxy groups having from 1 to 4 carbon atoms; and hydroxy groups.

4. The method of claim 1, wherein $R^1$ and $R^2$ together form a group of formula $$-CR^4=CR^5-CR^6=CR^7-,$$

in which $R^4$, $R^5$, $R^6$ and $R^7$ are independently selected from the group consisting of hydrogen atoms, halogen atoms, alkyl groups having from 1 to 3 carbon atoms, alkoxy groups having from 1 to 3 carbon atoms, trifluoromethyl groups and hydroxy groups.

5. The method of claim 1, wherein $R^1$ represents a hydrogen atom, a halogen atom or an alkyl group having from 1 to 3 carbon atoms;

$R^2$ represents a hydrogen atom; an alkyl group having from 1 to 3 carbon atoms; a phenyl group which is unsubstituted or which is substituted by at least one of substituents (a'), defined below; or said heterocyclic group being unsubstituted or being substituted by at least one of substituents (a'), defined below;

substituents (a'):
halogen atoms; alkyl groups having from 1 to 4 carbon atoms; alkoxy groups having from 1 to 4 carbon atoms; and hydroxy groups; and $R^3$ represents a quinuclidinyl group.

6. The method of claim 1, wherein $R^1$ represents a hydrogen atom or a halogen atom.

7. The method of claim 1, wherein $R^2$ represents a hydrogen atom; a phenyl group which is unsubstituted or which is substituted by at least one of substituents (a"), defined below; or said heterocyclic group being unsubstituted or being substituted by at least one of substituents (a"), defined below;

substituents (a"):
halogen atoms; alkoxy groups having from 1 to 4 carbon atoms; and hydroxy groups.

8. The method of claim 1, wherein $R^1$ and $R^2$ together form a group of formula $$-CR^4=CR^5-CR^6=CR^7-,$$

in which $R^4$, $R^5$, $R^6$ and $R^7$ are independently selected from the group consisting of hydrogen atoms, halogen atoms and hydroxy groups.

9. The method of claim 1, wherein $R^1$ represents a hydrogen atom or a halogen atom;

$R^2$ represents a hydrogen atom; a phenyl group which is unsubstituted or which is substituted by at least one of substituents (a"), defined below; or said heterocyclic group being unsubstituted or being substituted by at least one of substituents (a"), defined below;

substituents (a"):
halogen atoms; alkoxy groups having from 1 to 4 carbon atoms; and hydroxy groups; and $R^3$ represents a quinuclidinyl group.

10. The method of claim 1, wherein $R^1$ represents a hydrogen atom, a halogen atom or an alkyl group having from 1 to 3 carbon atoms;

$R^2$ represents a hydrogen atom; an alkyl group having from 1 to 3 carbon atoms; a phenyl group which is unsubstituted or which is substituted by at least one of substitutents (a'), defined below; or being unsubstituted or being substituted by at least one of substituents (a'), defined below;

substituents (a'):
halogen atoms; alkyl groups having from 1 to 4 carbon atoms; alkoxy groups having from 1 to 4 carbon atoms; and hydroxy groups;
or $R^1$ and $R^2$ together form a group of formula $$-CR^4=CR^5-CR^6=CR^7-,$$

in which $R^4$, $R^5$, $R^6$ and $R^7$ are independently selected from the group consisting of hydrogen atoms, halogen atoms, alkyl groups having from 1 to 3 carbon atoms, alkoxy groups having from 1 to 3 carbon atoms, trifluoromethyl groups and hydroxy groups; and $R^3$ represents a quinuclidinyl group.

11. The method of claim 1, wherein $R^1$ represents a hydrogen atom or a halogen atom;

$R^2$ represents a hydrogen atom; a phenyl group which is unsubstituted or which is substituted by at least one of substituents (a"), defined below; or being unsubstituted or being substituted by at least one of substituents (a"), defined below;

substituents (a"):
halogen atoms; alkoxy groups having from 1 to 4 carbon atoms; and hydroxy groups;
or $R^1$ and $R^2$ together form a group of formula $$-CR^4=CR^5-CR^6=CR^7-,$$

in which $R^4$, $R^5$, $R^6$ and $R^7$ are independently selected from the group consisting of hydrogen atoms, halogen atoms and hydroxy groups; and $R^3$ represents a quinuclidinyl group.

12. The method of claim 1, wherein the active compound is selected from the group consisting of:
3-(3-quinuclidinyloxy)isoxazole;
4-chloro-3-(3-quinuclidinyloxy)isoxazole;

4-chloro-3-(3-quinuclidinyloxy)-5-phenylisoxazole;
4-fluoro-5-methyl-3-(3-quinuclidinyloxy)isoxazole.
and pharmaceutically acceptable salts thereof.

13. A method for the treatment or prophylaxis of senile dementia in a mammal, comprising administering to said mammal a pharmaceutically effective amount of at least one active compound, wherein the active compound is selected from the group consisting of a compound of the following formula (I) and pharmaceutically acceptable salts thereof:

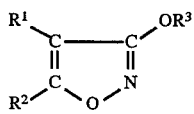
(I)

in which:

$R^1$ represents
a hydrogen atom,
a halogen atom or
an alkyl group having from 1 to 6 carbon atoms;

$R^2$ represents
a hydrogen atom,
an alkyl group having from 1 to 6 carbon atoms,
a phenyl group which is unsubstituted or which is substituted by at least one of substituent selected from the group consisting of
halogen atoms,
alkyl groups having from 1 to 6 carbon atoms,
alkoxy groups having from 1 to 6 carbon atoms,
alkylamino groups having from 1 to 4 carbon atoms,
dialkylamino groups in which each alkyl group has from 1 to 4 carbon atoms,
hydroxy groups,
nitro groups and
amino groups, or
a heterocyclic group selected from the group consisting of furyl, thienyl, pyrrolyl, pyridyl, thiazolyl, isothiazolyl, oxazolyl, isoxazolyl, imidazolyl, pyrazolyl, pyranyl, tetrahydrofuranyl, tetrahydrothienyl, pyrrolidinyl, thiazolidinyl, imidazolidinyl, imidazolinyl, oxazolinyl, oxazolidinyl, pyrazolidinyl, pyrrolidonyl, piperidonyl, oxazolidinyl, pyrazolidinyl, pyrrolidonyl, piperidonyl, pyridonyl, 2H-pyrrolyl, furazanyl and pyrazolinyl, said heterocyclic group being unsubstituted or being substituted by at least one substituent selected from the group consisting of
halogen atoms,
alkyl groups having from 1 to 6 carbon atoms,
alkoxy groups having from 1 to 6 carbon atoms,
alkylamino groups having from 1 to 4 carbon atoms,
dialkylamino groups in which each alkyl group has from 1 to 4 carbon atoms,
hydroxy groups,
nitro groups and
amino groups; or $R^1$ and $R^2$ together form a group of formula —$CR^4$=$CR^5$—$CR^6$=$CR^7$—, in which $R^4$, $R^5$, $R^6$ and $R^7$ are independently selected from the group consisting of
a hydrogen atom,
halogen atoms,
alkyl groups having from 1 to 6 carbon atoms,
alkoxy groups having from 1 to 4 carbon atoms,
halomethyl groups,
alkylamino groups having from 1 to 4 carbon atoms,
dialkylamino groups in which each alkyl group has from 1 to 4 carbon atoms,
hydroxy groups,
nitro groups,
aliphatic carboxylic acylamino groups having from 2 to 4 carbon atoms and
amino groups; and $R^3$ represents a quinuclidinyl group.

14. The method of claim 13, wherein $R^1$ represents a hydrogen atom, a halogen atom or an alkyl group having from 1 to 3 carbon atoms;

$R^2$ represents a hydrogen atom; an alkyl group having from 1 to 3 carbon atoms; a phenyl group which is unsubstituted or which is substituted by at least one of substituents (a'), defined below; or being unsubstituted or being substituted by at least one of substituents (a'), defined below;

substituents (a'):
halogen atoms; alkyl groups having from 1 to 4 carbon atoms; alkoxy groups having from 1 to 4 carbon atoms; and hydroxy groups;

or $R^1$ and $R^2$ together form a group of formula

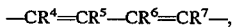

in which $R^4$, $R^5$, $R^6$ and $R^7$ are independently selected from the group consisting of hydrogen atoms, halogen atoms, alkyl groups having from 1 to 3 carbon atoms, alkoxy groups having from 1 to 3 carbon atoms, trifluoromethyl groups and hydroxy groups; and $R^3$ represents a quinuclidinyl group.

15. The method of claim 13, wherein $R^1$ represents a hydrogen atom or a halogen atom;

$R^2$ represents a hydrogen atom; a phenyl group which is unsubstituted or which is substituted by at least one of substituents (a"), defined below; or said heterocyclic group being unsubstituted or being substituted by at least one of substituents (a"), defined below;

substituents (a"):
halogen atoms; alkoxy groups having from 1 to 4 carbon atoms; and hydroxy groups;

or $R^1$ and $R^2$ together form a group of formula

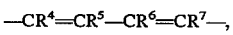

in which $R^4$, $R^5$, $R^6$ and $R^7$ are independently selected from the group consisting of hydrogen atoms, halogen atoms and hydroxy groups; and $R^3$ represents a quinuclidinyl group.

16. The method of claim 13, wherein said senile dementia is Alzheimer's disease.

17. The method of claim 13, wherein $R^1$ represents a hydrogen atom, a halogen atom or an alkyl group having from 1 to 3 carbon atoms.

18. The method of claim 13, wherein $R^2$ represents a hydrogen atom; an alkyl group having from 1 to 3 carbon atoms; a phenyl group which is unsubstituted or which is substituted by at least one of substituent selected from the group consisting of halogen atoms, alkyl groups having 1 to 4 carbon atoms, alkoxy groups having 1 to 4 carbon atoms and hydroxy groups; or said heterocyclic group being unsubstituted or being substituted by at least one of substituent selected from the group consisting of halogen atoms, alkyl groups having from 1 to 4 carbon atoms, alkoxy groups having from 1 to 4 carbon atoms and hydroxy groups.

19. The method of claim 13, wherein $R^1$ and $R^2$ together form a group of formula —$CR^4$=$CR^5$—$CR^6$=$CR^7$—, in which $R^4$, $R^5$, $R^6$ and $R^7$ are independently selected from the group consisting of hydrogen atoms, halogen atoms, alkyl groups having from 1 to 3 carbon atoms, alkoxy groups having from 1 to 3 carbon atoms, trifluoromethyl groups and hydroxy groups.

20. The method of claim 13, wherein
$R^1$ represents a hydrogen atom, a halogen atom or an alkyl group having from 1 to 3 carbon atoms;
$R^2$ represents a hydrogen atom; an alkyl group having from 1 to 3 carbon atoms; a phenyl group which is unsubstituted or which is substituted by at least one substituent selected from the group consisting of halogen atoms, alkyl groups having 1 to 4 carbon atoms, alkoxy groups having 1 to 4 carbon atoms and hydroxy groups; or said heterocyclic group being unsubstituted or being substituted by at least one of substituent selected from the group consisting of halogen atom, alkyl groups having from 1 to 4 carbon atoms, alkoxy groups having from 1 to 4 carbon atoms and hydroxy groups.

21. The method of claim 13, wherein $R^1$ represents a hydrogen atom or a halogen atom.

22. The method of claim 13, wherein $R^2$ represents a hydrogen atom; a phenyl group which is unsubstituted or which is substituted by at least one substituent selected from the group consisting of halogen atoms, alkoxy groups having 1 to 4 carbon atoms and hydroxy groups; or said heterocyclic group being unsubstituted or being substituted by at least one of substituent selected from the group consisting of halogen atoms, alkoxy groups having from 1 to 4 carbon atoms and hydroxy groups.

23. The method of claim 13, wherein $R^1$ and $R^2$ together form a group of formula —$CR^4$=$CR^5$—$CR^6$=$CR^7$—, in which $R^4$, $R^5$, $R^6$ and $R^7$ are independently selected from the group consisting of hydrogen atoms, halogen atoms and hydroxy groups.

24. The method of claim 13, wherein:
$R^1$ represents a hydrogen atom or a halogen atom;
$R^2$ represents a hydrogen atom; a phenyl group which is unsubstituted or which is substituted by at least one substituent selected from the group consisting of halogen atoms, alkoxy groups having from 1 to 4 carbon atoms and hydroxy groups; or said heterocyclic group being unsubstituted or being substituted by at least one substituent selected from the group consisting of halogen atoms, alkoxy groups having 1 to 4 carbon atoms and hydroxy groups.

25. The method of claim 1, wherein the compound is R-(−)-3-(3-quinuclidinyloxy)isoxazole hydrochloride.

26. The method of claim 13, wherein the compound is R-(−)-3-(3-quinuclidinyloxy)isoxazole hydrochloride.

27. A compound of formula (I):

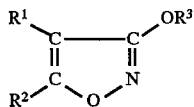

in which:
$R^1$ represents
a hydrogen atom,
a halogen atom or
an alkyl group having from 1 to 6 carbon atoms;
$R^2$ represents a heterocyclic group selected from the group consisting of furyl, thienyl, pyrrolyl, pyridyl, thiazolyl, isothiazolyl, oxazolyl, isoxazolyl, imidazolyl, pyrazolyl, pyranyl, tetrahydrofuranyl, tetrahydrothienyl, pyrrolidinyl, thiazolidinyl, imidazolidinyl, imidazolinyl, oxazolinyl, oxazolidinyl, pyrazolidinyl, pyrrolidonyl, piperiodonyl, pyridonyl, 2H-pyrrolyl, furazanyl and pyrazolinyl, said heterocyclic group being unsubstituted or being substituted by at least one substituent selected from the group consisting of
halogen atoms,
alkyl groups having from 1 to 6 carbon atoms,
alkoxy groups having from 1 to 6 carbon atoms,
alkylamino groups having from 1 to 4 carbon atoms,
dialkylamino groups in which each alkyl group has from 1 to 4 carbon atoms,
hydroxy groups,
nitro groups and
amino groups; and
$R^3$ represents a quinuclidinyl group, and pharmaceutically acceptable salts thereof.

28. The method of claim 27, wherein $R^1$ is a hydrogen atom or a halogen atom.

29. A method for the treatment or prophylaxis of anxiety, depression or psychosis in a mammal, comprising administering to said mammal a pharmaceutically effective amount of at least one active compound, wherein the active compound is selected from the group consisting of compounds of the following formula (I′) and pharmaceutically acceptable salts thereof:

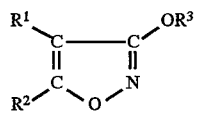

in which:
$R^1$ represents a hydrogen atom, a halogen atom or an alkyl group having from 1 to 6 carbon atoms;
$R^2$ represents a heterocyclic group selected from the group consisting of furyl, thienyl, pyrrolyl, pyridyl, thiazolyl, isothiazolyl, oxazolyl, isoxazolyl, imidazolyl, pyrazolyl, pyranyl, tetrahydrofuranyl, tetrahydrothienyl, pyrrolidinyl, thiazolidinyl, imidazolidinyl, imidazolinyl, oxazolinyl, oxazolidinyl, pyrazolidinyl, pyrrolidonyl, piperidonyl; pyridonyl, 2H-pyrrolyl, furazanyl and pyrazolinyl, said heterocyclic group being unsubstituted or being substituted by at least one substituent selected from the group consisting of halogen atoms; alkyl groups having from 1 to 6 carbon atoms; alkoxy groups having from 1 to 6 carbon atoms; alkylamino groups having from 1 to 4 carbon atoms; dialkylamino groups in which each alkyl group has from 1 to 4 carbon atoms; hydroxy groups; nitro groups; and amino groups; and
$R^3$ represents a quinuclidinyl group.

30. The method of claim 29, wherein the active compound is selected from the group consisting of R-(+)-3-(3-quinuclidinyloxy) isoxazole and pharmaceutically acceptable salts thereof.

31. A method for the treatment of prophylaxis of senile dementia in a mammal, comprising administering to said mammal a pharmaceutically effective amount of at least one active compound, wherein the active compound is selected from the group consisting of compounds of the following formula (I′) pharmaceutically acceptable salts thereof

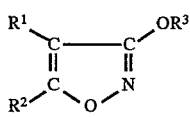

in which:

R[1] represents a hydrogen atom, a halogen atom or an alkyl group having from 1 to 6 carbon atoms;

R[2] represents a heterocyclic group selected from the group consisting of furyl, thienyl, pyrrolyl, pyridyl, thiazolyl, isothiazolyl, oxazolyl, isoxazolyl, imidazolyl, pyrazolyl, pyranyl, tetrahydrofuranyl, tetrahydrothienyl, pyrrolidinyl, thiazolidinyl, imidazolidinyl, imidazolinyl, oxazolinyl, oxazolidinyl, pyrazolidinyl, pyrrolidonyl, piperidonyl; pyridonyl, 2H-pyrrolyl, furazanyl and pyrazolinyl, said heterocyclic group being unsubstituted or being substituted by at least one substituent selected from the group consisting of halogen atoms; alkyl groups having from 1 to 6 carbon atoms; alkoxy groups having from 1 to 6 carbon atoms; alkylamino groups having from 1 to 4 carbon atoms; dialkylamino groups in which each alkyl group has from 1 to 4 carbon atoms; hydroxy groups; nitro groups; and amino groups; and R[3] represents a quinuclidinyl group.

32. The method of claim 31, wherein the active compound is selected from the group consisting of:
3-(3-quinuclidinyloxy)isoxazole;
4-chloro-3-(3-quinuclidinyloxy)isoxazole;
4-chloro-3-(3-quinuclidinyloxy)-5-phenylisoxazole;
4-fluoro-5-methyl-3-(3-quinoclidinyloxy)isoxazole and pharmaceutically acceptable salts thereof.

33. The method of claim 31, wherein the active compound is selected from the group consisting of R-(+)-3-(3-quinuclidinyloxy) isoxazole and pharmaceutically acceptable salts thereof.

34. The method of claim 31, wherein said senile dementia is Alzheimer's disease.

35. A compound of the formula

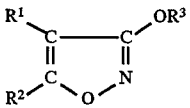

wherein
R[1] is a hydrogen atom or a halogen atom,
R[2] is a hydrogen atom or a $C_1$–$C_6$ alkyl group, and
R[3] is a quinuclidinyl group; and
pharmaceutically acceptable salts thereof.

36. A compound of claim 35, selected from the group consisting of 3-(3-quinuclidinyloxy)isoxazole, 4-chloro-5-methyl-3-(3-quinuclidinyloxy)isoxazole, 4-fluoro-5-methyl-3-(3-quinuclidinyloxy)isoxazole, and pharmaceutically acceptable salts thereof.

37. The compound of claim 35, selected from the group consisting of 4-fluoro-5-methyl-3-(3-quinuclidinyloxy)-isoxazole and pharmaceutically acceptable salts thereof.

38. The compound of claim 35, selected from the group consisting of 4-chloro-5-methyl-3-(3-quinuclidinyloxy)-isoxazole and pharmaceutically acceptable salts thereof.

39. The compound of claim 35, selected from the group consisting of R-(+)-3-(3-quinuclidinyloxy)isoxazole and pharmaceutically acceptable salts thereof.

40. The compound of claim 35, wherein the compound is R-(−)-3-(3-quinuclidinyloxy)isoxazole hydrochloride.

41. A pharmaceutical composition for the treatment or prophylaxis of anxiety, depression, psychosis or senile dementia comprising a pharmaceutically effective amount of at least one compound of claim 35 or a pharmaceutically acceptable salt thereof, in admixture with a pharmaceutically acceptable carrier or diluent.

42. The composition of claim 41, wherein the compound is selected from the group consisting of 3-(3-quinuclidinyloxy)isoxazole, 4-chloro-5-methyl-3-(3-quinuclidinyloxy)isoxazole, 4-fluoro-5-methyl-3-(3-quinuclidinyloxy)isoxazole, and pharmaceutically acceptable salts thereof.

43. The composition of claim 41, wherein the active compound is selected from the group consisting of R-(+)-3-(3-quinuclidinyloxy)isoxazole and pharmaceutically acceptable salts thereof.

44. The composition of claim 41, wherein the compound is R-(−)-3-(3-quinuclidinyloxy)isoxazole hydrochloride.

45. The compound of claim 35, selected from the group consisting of 3-(3-quinuclidinyloxy)isoxazole and pharmaceutically acceptable salts thereof.

46. The compound of claim 35, selected from the group consisting of R-(+)-3-(3-quinuclidinyloxy)isoxazole and pharmaceutically acceptable salts thereof.

47. The compound of claim 35, selected from the group consisting of S-(−)-3-(3-quinuclidinyloxy)isoxazole and pharmaceutically acceptable salts thereof.

48. The compound of claim 35, selected from the group consisting of 4-chloro-3-(3-quinuclidinyloxy)isoxazole and pharmaceutically acceptable salts thereof.

* * * * *